US010525268B2

United States Patent
Torgerson

(10) Patent No.: US 10,525,268 B2
(45) Date of Patent: Jan. 7, 2020

(54) DELIVERY OF INDEPENDENT INTERLEAVED PROGRAMS TO PRODUCE HIGHER-FREQUENCY ELECTRICAL STIMULATION THERAPY

(71) Applicant: Medtronic, Inc., Minneapolis, MN (US)

(72) Inventor: Nathan A. Torgerson, Andover, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 125 days.

(21) Appl. No.: 15/623,141

(22) Filed: Jun. 14, 2017

(65) Prior Publication Data

US 2018/0056073 A1    Mar. 1, 2018

Related U.S. Application Data

(60) Provisional application No. 62/378,544, filed on Aug. 23, 2016.

(51) Int. Cl.
*A61N 1/36* (2006.01)
*A61N 1/02* (2006.01)
(Continued)

(52) U.S. Cl.
CPC ......... *A61N 1/36185* (2013.01); *A61N 1/025* (2013.01); *A61N 1/0553* (2013.01);
(Continued)

(58) Field of Classification Search
CPC . A61N 1/18; A61N 1/32; A61N 1/323; A61N 1/36; A61N 1/3603; A61N 1/36034;
(Continued)

(56) References Cited

U.S. PATENT DOCUMENTS 5,603,726 A    2/1997    Schulman et al.
5,800,465 A    9/1998    Thompson et al.
(Continued)

FOREIGN PATENT DOCUMENTS

CN    102921105 B    8/2015
CN    107050645 A    8/2017
(Continued)

OTHER PUBLICATIONS

International Search Report and Written Opinion from International Application No. PCT/US2017/037610, dated Nov. 2, 2017, 16 pp.
(Continued)

*Primary Examiner* — Allen Porter
(74) *Attorney, Agent, or Firm* — Shumaker & Sieffert, P.A.

(57) ABSTRACT

The techniques of the disclosure describe example medical devices, systems, and methods for interleaving a plurality of low-frequency electrical stimulation pulse trains delivered by a plurality of sets of electrodes of an implantable medical device (IMD) to effectively deliver a combined high-frequency electrical pulse train to a target tissue area. In one example, each set of the plurality of sets of electrodes has a unique anode and cathode. In another example, a clinician adjusts the size or shape of the target tissue area receiving the combined high-frequency electrical pulse train by selecting different combinations of the plurality of sets of electrodes.

22 Claims, 10 Drawing Sheets

(51) Int. Cl.
  *A61N 1/05* (2006.01)
  *A61N 1/06* (2006.01)
  *A61N 1/372* (2006.01)
  *A61N 1/375* (2006.01)

(52) U.S. Cl.
  CPC ........... *A61N 1/06* (2013.01); *A61N 1/36071* (2013.01); *A61N 1/36135* (2013.01); *A61N 1/36153* (2013.01); *A61N 1/36157* (2013.01); *A61N 1/36171* (2013.01); *A61N 1/36175* (2013.01); *A61N 1/36178* (2013.01); *A61N 1/37229* (2013.01); *A61N 1/37247* (2013.01); *A61N 1/3756* (2013.01)

(58) Field of Classification Search
  CPC .............. A61N 1/3605; A61N 1/36062; A61N 1/36167; A61N 1/36178
  See application file for complete search history.

(56) References Cited

U.S. PATENT DOCUMENTS

| | | |
|---|---|---|
| 6,289,247 B1 | 9/2001 | Faltys et al. |
| 6,314,325 B1 | 11/2001 | Fitz |
| 6,421,566 B1 | 7/2002 | Holsheimer |
| 6,505,078 B1 | 1/2003 | King et al. |
| 6,675,046 B2 | 1/2004 | Holsheimer |
| 6,850,802 B2 | 2/2005 | Holsheimer |
| 6,988,006 B2 | 1/2006 | King et al. |
| 7,333,858 B2 | 2/2008 | Killian et al. |
| 7,577,480 B2 | 8/2009 | Zeijlemaker |
| 7,657,318 B2 | 2/2010 | King et al. |
| 7,689,289 B2 | 3/2010 | King |
| 7,742,810 B2 | 6/2010 | Moffitt et al. |
| 8,359,103 B2 | 1/2013 | Alataris et al. |
| 8,504,150 B2 | 8/2013 | Skelton |
| 8,620,441 B2 | 12/2013 | Greenberg et al. |
| 8,694,108 B2 | 4/2014 | Alataris et al. |
| 8,708,934 B2 | 4/2014 | Skelton et al. |
| 8,712,533 B2 | 4/2014 | Alataris et al. |
| 8,712,534 B2 | 4/2014 | Wei |
| 9,002,460 B2 | 4/2015 | Parker |
| 9,138,582 B2 | 9/2015 | Doan et al. |
| 9,155,892 B2 | 10/2015 | Parker et al. |
| 9,339,655 B2 | 5/2016 | Carbunaru |
| 9,381,356 B2 | 7/2016 | Parker et al. |
| 9,386,934 B2 | 7/2016 | Parker et al. |
| 2004/0267333 A1 | 12/2004 | Kronberg |
| 2007/0067004 A1 | 3/2007 | Boveja et al. |
| 2008/0221640 A1 | 9/2008 | Overstreet et al. |
| 2009/0036945 A1 | 2/2009 | Chancellor et al. |
| 2009/0222053 A1 | 9/2009 | Gaunt et al. |
| 2011/0054570 A1 | 3/2011 | Lane |
| 2011/0071589 A1 | 3/2011 | Starkebaum et al. |
| 2011/0125223 A1 | 5/2011 | Carbunaru et al. |
| 2011/0282412 A1 | 11/2011 | Glukhovsky et al. |
| 2012/0130444 A1 | 5/2012 | Wei et al. |
| 2012/0155188 A1 | 6/2012 | Buettner et al. |
| 2012/0296389 A1 | 11/2012 | Fang et al. |
| 2013/0060301 A1 | 3/2013 | Polefko et al. |
| 2013/0110194 A1 | 5/2013 | Wei et al. |
| 2013/0208390 A1 | 8/2013 | Singh et al. |
| 2013/0268021 A1 | 10/2013 | Moffitt |
| 2013/0289664 A1 | 10/2013 | Johanek |
| 2014/0005753 A1* | 1/2014 | Carbunaru ......... A61N 1/36189 607/62 |
| 2014/0025146 A1 | 1/2014 | Alataris et al. |
| 2014/0031896 A1 | 1/2014 | Alataris et al. |
| 2014/0031905 A1 | 1/2014 | Irazoqui et al. |
| 2014/0074189 A1 | 3/2014 | Moffitt |
| 2014/0142656 A1 | 5/2014 | Alataris et al. |
| 2014/0142673 A1 | 5/2014 | Alataris et al. |
| 2014/0243924 A1 | 8/2014 | Zhu et al. |
| 2014/0243926 A1 | 8/2014 | Carcieri |
| 2014/0277281 A1* | 9/2014 | Grandhe ............ A61N 1/36146 607/59 |
| 2014/0296936 A1 | 10/2014 | Alataris et al. |
| 2014/0364920 A1* | 12/2014 | Doan ................. A61N 1/36071 607/46 |
| 2014/0371813 A1 | 12/2014 | King et al. |
| 2014/0378941 A1 | 12/2014 | Su et al. |
| 2014/0379043 A1 | 12/2014 | Howard |
| 2015/0127062 A1 | 5/2015 | Holley et al. |
| 2015/0179177 A1 | 6/2015 | Nagao |
| 2015/0360031 A1 | 12/2015 | Bornzin et al. |
| 2016/0030741 A1 | 2/2016 | Wei et al. |
| 2016/0082265 A1 | 3/2016 | Moffitt et al. |
| 2016/0114166 A1 | 4/2016 | Kaula et al. |
| 2016/0121124 A1 | 5/2016 | Johanek et al. |
| 2016/0136420 A1 | 5/2016 | Brink et al. |
| 2016/0157769 A1 | 6/2016 | Min et al. |
| 2016/0175594 A1 | 6/2016 | Min et al. |
| 2016/0271413 A1* | 9/2016 | Vallejo ................ A61N 2/008 |
| 2017/0209695 A1 | 7/2017 | Solomon |
| 2018/0056073 A1 | 3/2018 | Torgerson |

FOREIGN PATENT DOCUMENTS

| | | |
|---|---|---|
| EP | 2396072 B1 | 3/2013 |
| WO | 2002009808 A1 | 2/2002 |
| WO | 2010058178 A1 | 5/2010 |
| WO | 2010123704 A | 10/2010 |
| WO | 2011156286 A2 | 12/2011 |
| WO | 2015143509 A1 | 1/2015 |
| WO | 2015179177 A1 | 11/2015 |
| WO | 2015179281 A1 | 11/2015 |
| WO | 2016090420 A1 | 6/2016 |
| WO | 2017106503 A1 | 6/2017 |

OTHER PUBLICATIONS

"St. Jude's Prodigy Neurostimulator with Burst Technology," Medgadget, Mar. 20, 2014, 4 pp.

Abejon et al., "Back pain coverage with spinal cord stimulation: A different treatment for each patient," International Neuromodulation Society. Jun. 10, 2015; 567, Abstract Only, 1 pp.

Abeloos, et al., "High density stimulation as an alternative to uncomfortable cervical tonic spinal cord stimulation: case report," International Neuromodulation Society 12th World Congress, Jun. 11-15, 2015, Abstract Only, 1 pp.

Breel, et al., "High Density Stimulation: A novel programming paradigm for the treatment of chronic pain," International Neuromodulation Society (INS) 12th World Congress; Jun. 9, 2015, Abstract Only, 1 pp.

Cuellar MD et al., "Effect of high-frequency alternating current on spinal afferent nociceptive transmission," Neuromodulation: Technology at the Neural Interface; Jul.-Aug. 2013;16(4): pp. 318-327.

Cui, et al., "Effect of spinal cord stimulation on tactile hypersensitivity in mononeuropathic rats is potentiated by simultaneous GABA(B) and adenosine receptor activation," Neuroscience Letters 247: Apr. 1998; pp. 183-186.

Cui et al., "Spinal cord stimulation attenuates augmented dorsal horn release of excitatory amino acids in mononeuropathy via a GABAergic mechanism," Pain 73, Oct. 1997, pp. 87-95.

De Ridder, et al., "Burst spinal cord stimulation for limb and back pain," World neurosurgery, Nov. 2013; 80 (5):642-649 e641.

De Ridder, et al., "Burst spinal cord stimulation: toward paresthesia-free pain suppression," Neurosurgery. May 2010; 66(5): 986-990.

Downey, "Asynchronous Neuromuscular Electrical Stimulation," University of Florida, 2015, accessed on Jul. 18, 2016, 107 pp.

Duyvendak, MD, et al., "High density stimulation: a novel programming paradigm for the treatment of chronic back and leg pain," Abstracts, International Neuromodulation Society 12th World Congress: Jun. 11-15, 2015, 1 pp.

Gao et al., "Effects of spinal cord stimulation with "standard clinical" and higher frequencies on peripheral blood flow in rats," Brain Res. Feb. 8 2010;1313: pp. 53-61.

Grider, et al., "High Frequency (1000 Hz) Stimulation Using Commercially Available Implantable Pulse Generator," North American Neuromodulation Society. Dec. 2013, Abstract Only, 2 pp.

(56) References Cited

OTHER PUBLICATIONS

Guan et al., "Spinal cord stimulation-induced analgesia: electrical stimulation of dorsal column and dorsal roots attenuates dorsal horn neuronal excitability in neuropathic rats," Anesthesiology. Dec. 2010;113(6): pp. 1392-1405.
Guan et al., "Spinal Cord Stimulation: Neurophysiological and Neurochemical Mechanisms of Action" Curr Pain Headache Rep DOI 10,1007s11916-014-0260-4, Mar. 2012, pp. 217-225.
Holsheimer, "Computer modelling of spinal cord stimulation and its contribution to therapeutic efficacy," Spinal Cord Aug. 1998, 36: pp. 531-540.
Hunt SP, Mantyh PW. The molecular dynamics of pain control. Nat Rev Neurosci. Feb. 2001;2(2):83-91.
Kemler, et al., "Spinal cord stimulation in patients with chronic reflex sympathetic dystrophy," N Engl J Med, Aug. 31, 2000; 343(9):618-624.
Kilgore, PhD, et al., "Reversible Nerve Conduction Block Using Kilohertz Frequency Alternating Current," Neuromodulation. Aug. 2013, pp. 242-255.
Kumar, et al., "Spinal cord stimulation versus conventional medical management for neuropathic pain: a multicentre randomised controlled trial in patients with failed back surgery syndrome," Pain Jul. 2007; 132(1-2): 179-188.
Likar et al., "High density spinal cord stimulation: a multi-center experience," Abstracts, International Neuromodulation Society 12th World Congress; Jun. 11-15, 2015, 1 pp.
Sweet et al., "High Frequency vs. Burst Stimulation Patterns for Dorsal Column Stimulation: The Importance of Charge," American Association of Neurological Surgeons, Abstract, Apr. 4, 2014, 2 pp.
Maeda, et al., "Low frequencies, but not high frequencies of bi-polar spinal cord stimulation reduce cutaneous and muscle hyperalgesia induced by nerve injury," Pain; Feb. 2008; 138(1): pp. 143-152.
North M.D. et al., "Spinal cord stimulation versus repeated lumbosacral spine surgery for chronic pain: a randomized, controlled trial," Neurosurgery, Jan. 2005; 56(1): 98-106; discussion 106-107.
North, et al., "Clinical outcomes of 1 kHz subperception spinal cord stimulation (SCS): Results of a prospective randomized controlled crossover trial," Abstracts, International Neuromodulation Society, Jun. 2015, 1 pp.
Ranck, Jr., et al., "Which elements are excited in electrical stimulation of mammalian central nervous system: a review," Brain Res. Nov. 21, 1975; 98(3): pp. 417-440.
Replogle, MD., et al., "Case Series Comparing Moderate (1000 Hz) Versus Conventional Frequency Stimulation During Spinal Cord Stimulator Trials," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.
Sato, et al., "Spinal cord stimulation reduces hypersensitivity through activation of opioid receptors in a frequency-dependent manner," Eur J Pain. Apr. 17, 2012 (4): pp. 551-561.
Song, et al., "Efficacy of kilohertz-frequency and conventional spinal cord stimulation in rat models of different pain conditions," Neuromodulation Jan. 2014; 17(3): pp. 226-234.
Schu et al., "A prospective, randomised, double-blind, placebo-controlled study to examine the effectiveness of burst spinal cord stimulation patterns for the treatment of failed back surgery syndrome," Neuromodulation. Apr. 2014; 17 (5): pp. 443-450.
Shechter et al., "Conventional and kilohertz-frequency spinal cord stimulation produces intensity- and frequency-dependent inhibition of mechnical hypersensitivity in a rat model of neuropathic pain," Anesthesiology, Aug. 2013; 119(2): pp. 422-432.
Youn et al., "The Effect of High Frequency Stimulation on Sensory Thresholds in Chronic Pain Patients," North American Neuromodulation Society. 2014, 1 pp. Applicant points out in accordance with MPEP 609.04(a) that the 2005 year of publication is sufficiently earlier than the effective U.S. filing date of the present application, and any foreign priority date that the particular month of publication is not in issue.
Maeda, et al., "Increased c-fos immunoreactivity in the spinal cord and brain following spinal cord stimulation is frequency-dependent," Brain Res. Mar. 9, 2009;1259: pp. 40-50.
Sluka, et al., "High-frequency, but not low-frequency, transcutaneous electrical nerve stimulation reduces aspartate and glutamate release in the spinal cord dorsal horn," J Neurochem. Oct. 17, 2005; 95(6); pp. 1794-1801.
Smith, et al., "Successful use of high-frequency spinal cord stimulation following traditional treatment failure," Stereotact Funct Neurosurg. Apr. 2015; 93(3): pp. 190-193.
Wille, MD, et al., "Altering Conventional to High Density Spinal Cord Stimulation: An Energy Dose-Response Relationship in Neuropathic Pain Therapy," Neuromodulation: Technology at the Neural Interface, Aug. 2016, 9 pp.
Invitation to Pay Additional Fees and Partial International Search Report from International Application No. PCT/US2017/037610, dated Sep. 6, 2017, 12 pp.
Bhadra et al., "High frequency electrical conduction block of the pudendal nerve," Journal of Neural Eng., IOP Publishing LTD, published Jun. 3, 2006,14 pp.
Boger et al., "Bladder Voiding by Combined High Frequency Electrical Pudendal Nerve Block and Sacral Root Stimulation," Neurourology and Urodynamics, Wiley InterScience, vol. 27, Issue 5, Jul. 2, 2008, 6 pp.
Hubscher, et al., "Convergence and cross talk in urogenital neural circuitries," J. Neurophysiol 110: 1997-2005, first published Aug. 7, 2013, 9 pp.
Maggi, et al., "Effect of urethane anesthesia on the micturition reflex in capsaicin-treated rats." Journal of the Autonomic Nervous System, Jan. 1990, 30(3): 247-251.
Schu et al., "A prospective, randomised, double-blind, placebo-controlled study to examine the effectiveness of burst spinal cord stimulation patterns for the treatment of failed back surgery syndrome," Neuromodulation, Jun. 2014; 17 (5):443-450.
Snellings et al., "Effects of stimulation site and stimulation parameters on baldder inhibition by electrical nerve stimulation," BJU International, published Aug. 9, 2011, pp. 136-143.
Walter, et al., "Inhibiting the hyperreflexic bladder with electrical stimulation in a spinal animal model." Neurourology and Urodynamics, 1993, 12:241-253. Applicant points out in accordance with MPEP 609.04(a) that the 1993 year of publication is sufficiently earlier than the effective U.S. filing date of the present application, and any foreign priority date that the particular month of publication is not in issue.
Woock, et al., "Activation and inhibition of the micturition reflex by penile afferents in the cat," Am J. Physiol Regul Intergre Comp Physiol, published Apr. 23, 2008, pp. R1880-R1889.
Youn et al., "The Effect of High Frequency Stimulation on Sensory Thresholds in Chronic Pain Patients," North American Neuromodulation Society. 2014, 1 pp. Applicant points out in accordance with MPEP 609.04(a) that the 2014 year of publication is sufficiently earlier than the effective U.S. filing date of the present application, and any foreign priority date that the particular month of publication is not in issue.
International Preliminary Report on Patentability from International Application No. PCT/US2017/037610, dated Feb. 26, 2019, 9 pp.

\* cited by examiner

DELIVERY OF INDEPENDENT INTERLEAVED PROGRAMS TO PRODUCE HIGHER-FREQUENCY ELECTRICAL STIMULATION THERAPY

This application claims the benefit of U.S. Provisional Application No. 62/378,544 by Torgerson entitled, "DELIVERY OF INDEPENDENT INTERLEAVED PROGRAMS TO PRODUCE HIGHER-FREQUENCY ELECTRICAL STIMULATION THERAPY" and filed on Aug. 23, 2016, the entire content of which is incorporated herein by reference.

TECHNICAL FIELD

This disclosure generally relates to electrical stimulation therapy.

BACKGROUND

Medical devices may be external or implanted, and may be used to deliver electrical stimulation therapy to patients to various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes, a polarity of each selected electrode, a voltage or current amplitude, a pulse width, and a pulse frequency as stimulation parameters. A set of parameters, such as a set including electrode combination, electrode polarity, amplitude, pulse width and pulse rate, may be referred to as a program in the sense that they define the electrical stimulation therapy to be delivered to the patient.

SUMMARY

In general, the disclosure describes example medical devices, systems, and techniques for delivering a plurality of lower-frequency electrical stimulation therapy programs to a patient via a plurality of electrode combinations of an implantable medical device (IMD) on a time-interleaved basis to effectively deliver combined, higher-frequency electrical stimulation to a target tissue area.

In some examples, none of the electrodes in the electrode combinations are common with one another. In particular, each combination of electrodes is unique, having a unique anode and a unique cathode, such that the same electrode is not used in any of the combinations of electrodes. In some examples, at least two of a plurality of two or more electrode combinations do not have electrodes in common with one another, wherein some electrode combinations may have electrodes in common with one another.

In some examples, a clinician may adjust the size or shape of the target tissue area receiving the high-frequency electrical stimulation by selecting different combinations of the plurality of sets of electrodes. By interleaving the pulses of the plurality of low-frequency electrical stimulation pulse trains to deliver a combined high-frequency pulse train to the target tissue area, an IMD may effectively deliver a high-frequency electrical stimulation program to a target tissue area.

Accordingly, the techniques of the disclosure allow an IMD to deliver higher frequency stimulation using interleaved low-frequency electrical stimulation therapy programs. By combining the time-interleaved, low-frequency electrical stimulation therapy programs, such an IMD may effectively provide stimulation at higher frequencies to target tissue, while tissue near each the electrodes selected for each program receive lower frequency stimulation, and thereby less energy.

In one example, this disclosure describes a method including: generating first electrical stimulation pulses at a first frequency greater than approximately 600 Hertz and less than approximately 1,500 Hertz; generating second electrical stimulation pulses at a second frequency greater than approximately 600 Hertz, less than approximately 1,500 Hertz, and on a time-interleaved basis with the first electrical stimulation pulses such that the first and second stimulation pulses form a combined pulse train with a combined pulse frequency of greater than approximately 1,500 Hertz; delivering the first electrical stimulation pulses to a patient via a first combination of electrodes including at least one anodic electrode and at least one cathodic electrode; and delivering the second electrical stimulation pulses to a patient via a second combination of electrodes including at least one anodic electrode and at least one cathodic electrode, wherein none of the second combination of electrodes are common with any of the electrodes of the first combination of electrodes.

In another example, this disclosure describes a method comprising: receiving, by an implantable medical device (IMD) and from an external programmer, a first selection of a first target tissue of a patient; determining, by the IMD and in response to the first selection, a first set of electrode combinations connected to the IMD via a first plurality of leads, delivering, by the IMD and to the first target tissue, a first plurality of electrical stimulation pulse trains comprising electrical stimulation pulse trains delivered from a first electrode combination of the first set of electrode combinations time-interleaved with electrical stimulation pulse trains delivered from a second electrode combination of the first set of electrode combinations, wherein the first plurality of electrical stimulation pulse trains is delivered at a combined frequency that is higher than separate frequencies of each respective electrical stimulation pulse train delivered from the first electrode combination and the second electrode combination of the first set of electrode combinations; receiving, by an implantable medical device (IMD) and from an external programmer, a second selection of a second target tissue of a patient; determining, by the IMD and in response to the second selection, a second set of electrode combinations connected to the IMD via the plurality of leads, delivering, by the IMD and to the second target tissue, a second plurality of electrical stimulation pulse trains comprising electrical stimulation pulse trains delivered from a third electrode combination of the second set of electrode combinations time-interleaved with electrical stimulation pulse trains delivered from a fourth electrode combination of the second set of electrode combinations, wherein the second plurality of electrical stimulation pulse trains is delivered at a combined frequency that is higher than separate frequencies of each respective electrical stimulation pulse train delivered from the third electrode combination and the fourth electrode combination of the second set of electrode combinations; wherein the first set of electrode combinations comprises at least a first anode electrode and a first cathode electrode and the second set of electrode combinations comprises at least a second anode electrode and a second cathode electrode, and wherein the first anode, first cathode, second anode, and second cathode are different electrodes.

In another example, this disclosure describes a system including: at least one lead including: a first combination of electrodes including at least one anodic electrode and at least one cathodic electrode; and a second combination of electrodes including at least one anodic electrode and at least one cathodic electrode, wherein none of the second combination of electrodes are common with any of the electrodes of the first combination of electrodes; and an implantable medical device (IMD) including: stimulation generation circuitry configured to: generate first electrical stimulation pulses at a first frequency greater than approximately 600 Hertz and less than approximately 1,500 Hertz; and generate second electrical stimulation pulses at a second frequency greater than approximately 600 Hertz, less than approximately 1,500 Hertz, and on a time-interleaved basis with the first electrical stimulation pulses such that the first and second stimulation pulses form a combined pulse train with a combined pulse frequency of greater than approximately 1,500 Hertz; and processing circuitry configured to: control delivery of the first electrical stimulation pulses to a patient via the first combination of electrodes; and control delivery of the second electrical stimulation pulses to a patient via the second combination of electrodes.

In another example, this disclosure describes an implantable medical device (IMD) comprising: telemetry circuitry configured to receive, from an external programmer, a first selection of a first target tissue of a patient; and processing circuitry configured to: determine, in response to the first selection, a first set of electrode combinations connected to the IMD via a first plurality of leads; and control delivery via stimulation generation circuitry of the IMD and to the first target tissue, a first plurality of electrical stimulation pulse trains comprising electrical stimulation pulse trains delivered from a first electrode combination of the first set of electrode combinations time-interleaved with electrical stimulation pulse trains delivered from a second electrode combination of the first set of electrode combinations, wherein the first plurality of electrical stimulation pulse trains is delivered at a combined frequency that is higher than separate frequencies of each respective electrical stimulation pulse train delivered from the first electrode combination and the second electrode combination of the first set of electrode combinations; wherein the telemetry circuitry is further configured to receive, from the external programmer, a second selection of a second target tissue of a patient, and wherein the processing circuitry is further configured to: determine, in response to the second selection, a second set of electrode combinations connected to the IMD via a second plurality of leads; and control delivery via stimulation generation circuitry of the IMD and to the second target tissue, a second plurality of electrical stimulation pulse trains comprising electrical stimulation pulse trains delivered from a third electrode combination of the second set of electrode combinations time-interleaved with electrical stimulation pulse trains delivered from a fourth electrode combination of the second set of electrode combinations, wherein the second plurality of electrical stimulation pulse trains is delivered at a combined frequency that is higher than separate frequencies of each respective electrical stimulation pulse train delivered from the third electrode combination and the fourth electrode combination of the second set of electrode combinations, wherein the first set of electrode combinations comprises at least a first anode electrode and a first cathode electrode and the second set of electrode combinations comprises at least a second anode electrode and a second cathode electrode, and wherein the first anode, first cathode, second anode, and second cathode are different electrodes.

The details of one or more examples of the techniques of this disclosure are set forth in the accompanying drawings and the description below. Other features, objects, and advantages of the techniques will be apparent from the description and drawings, and from the claims.

DETAILED DESCRIPTION

Figure 1:
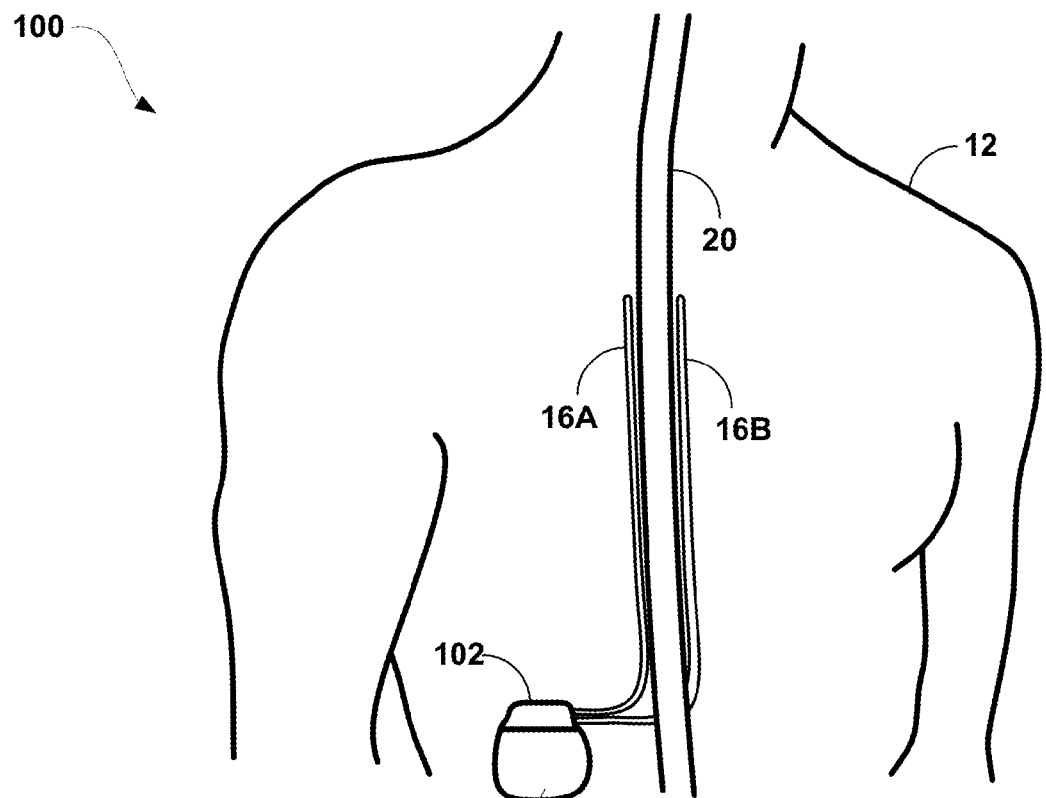
FIG. 1 is a conceptual diagram illustrating an example system that includes a medical device programmer and an implantable medical device (IMD) configured to deliver higher frequency electrical stimulation therapy to a patient using interleaved, lower frequency stimulation programs.

FIG. 1 is a conceptual diagram illustrating example system 100 that includes an implantable medical device (IMD) 102 configured to deliver electrical stimulation therapy to patient 12. In the example shown in FIG. 1, IMD 102 is configured to deliver SCS therapy. Although the techniques described in this disclosure are generally applicable to a variety of medical devices including external and implantable medical devices (IMDs), application of such techniques to IMDs and, more particularly, implantable electrical stimulators (e.g., neurostimulators) will be described for purposes of illustration. More particularly, the disclosure will refer to an implantable spinal cord stimulation (SCS) system for purposes of illustration, but without limitation as to other types of medical devices or other therapeutic applications of medical devices.

As shown in FIG. 1, system 100 includes an IMD 102, leads 16A, 16B, and external programmer 104 shown in conjunction with a patient 12, who is ordinarily a human patient. In the example of FIG. 1, IMD 102 is an implantable electrical stimulator that is configured to generate and deliver electrical stimulation therapy to patient 12 via electrodes of leads 16A, 16B, e.g., for relief of chronic pain or other symptoms. IMD 102 may be a chronic electrical stimulator that remains implanted within patient 12 for weeks, months, or even years. In other examples, IMD 102 may be a temporary, or trial, stimulator used to screen or evaluate the efficacy of electrical stimulation for chronic therapy. In one example, IMD 102 is implanted within patient 12, while in another example, IMD 102 is an external device coupled to percutaneously implanted leads. In some examples, IMD uses one or more leads, while in other examples, IMD 102 is leadless.

IMD 102 may be constructed of any polymer, metal, or composite material sufficient to house the components of IMD 102 (e.g., components illustrated in FIG. 2) within patient 12. In this example, IMD 102 may be constructed with a biocompatible housing, such as titanium or stainless steel, or a polymeric material such as silicone, polyurethane, or a liquid crystal polymer, and surgically implanted at a site in patient 12 near the pelvis, abdomen, or buttocks. In other examples, IMD 102 may be implanted within other suitable sites within patient 12, which may depend, for example, on the target site within patient 12 for the delivery of electrical stimulation therapy. The outer housing of IMD 102 may be configured to provide a hermetic seal for components, such as a rechargeable or non-rechargeable power source. In addition, in some examples, the outer housing of IMD 102 may be selected from a material that facilitates receiving energy to charge the rechargeable power source.

Electrical stimulation energy, which may be constant current or constant voltage based pulses, for example, is delivered from IMD 102 to one or more target tissue sites of patient 12 via one or more electrodes (not shown) of implantable leads 16A and 16B (collectively "leads 16"). In the example of FIG. 1, leads 16 carry electrodes that are placed adjacent to the target tissue of spinal cord 20. One or more of the electrodes may be disposed at a distal tip of a lead 16 and/or at other positions at intermediate points along the lead. Leads 16 may be implanted and coupled to IMD 102. The electrodes may transfer electrical stimulation generated by an electrical stimulation generator in IMD 102 to tissue of patient 12. Although leads 16 may each be a single lead, lead 16 may include a lead extension or other segments that may aid in implantation or positioning of lead 16. In some other examples, IMD 102 may be a leadless stimulator with one or more arrays of electrodes arranged on a housing of the stimulator rather than leads that extend from the housing. In addition, in some other examples, system 100 may include one lead or more than two leads, each coupled to IMD 102 and directed to similar or different target tissue sites.

The electrodes of leads 16 may be electrode pads on a paddle lead, circular (e.g., ring) electrodes surrounding the body of the lead, conformable electrodes, cuff electrodes, segmented electrodes (e.g., electrodes disposed at different circumferential positions around the lead instead of a continuous ring electrode), or any other type of electrodes capable of forming unipolar, bipolar or multipolar electrode combinations for therapy. Ring electrodes arranged at different axial positions at the distal ends of lead 16 will be described for purposes of illustration.

The deployment of electrodes via leads 16 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays may include electrode segments, which may be arranged at respective positions around a periphery of a lead, e.g., arranged in the form of one or more segmented rings around a circumference of a cylindrical lead.

The therapy parameters for a therapy program (also referred to herein as a set of electrical stimulation parameter values) that controls delivery of stimulation therapy by IMD 102 through the electrodes of leads 16 may include information identifying which electrodes have been selected for delivery of stimulation according to a stimulation program, the polarities of the selected electrodes, i.e., the electrode combination for the program, and voltage or current amplitude, pulse rate, and pulse width of stimulation delivered by the electrodes. Delivery of stimulation pulses will be described for purposes of illustration.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 12.

In some examples, lead 16 may include one or more sensors configured to allow IMD 102 to monitor one or more parameters of patient 12. The one or more sensors may be provided in addition to, or in place of, therapy delivery by lead 16.

IMD 102 is configured to deliver electrical stimulation therapy to patient 12 via selected combinations of electrodes carried by one or both of leads 16, alone or in combination with an electrode carried by or defined by an outer housing of IMD 102. The target tissue for the electrical stimulation therapy may be any tissue affected by electrical stimulation, which may be in the form of electrical stimulation pulses or continuous waveforms. In some examples, the target tissue includes nerves, smooth muscle or skeletal muscle. In the example illustrated by FIG. 1, the target tissue is tissue proximate spinal cord 20, such as within an intrathecal space or epidural space of spinal cord 20, or, in some examples, adjacent nerves that branch off of spinal cord 20. Leads 16 may be introduced into spinal cord 20 in via any suitable region, such as the thoracic, cervical or lumbar regions. Stimulation of spinal cord 20 may, for example, prevent pain signals from traveling through spinal cord 20 and to the brain of patient 12. Patient 12 may perceive the interruption of pain signals as a reduction in pain and, therefore, efficacious therapy results.

IMD 102 generates and delivers electrical stimulation therapy to a target stimulation site within patient 12 via the electrodes of leads 16 to patient 12 according to one or more therapy programs. A therapy program defines values for one or more parameters that define an aspect of the therapy delivered by IMD 102 according to that program. For example, a therapy program that controls delivery of stimulation by IMD 102 in the form of pulses may define values for voltage or current pulse amplitude, pulse width, and pulse rate for stimulation pulses delivered by IMD 102 according to that program.

Moreover, in some examples, IMD 102 delivers electrical stimulation therapy to patient 12 according to multiple therapy programs, which may be stored as a therapy program group. For example, as described below, in some examples, IMD 102 may deliver different pulses of electrical stimulation signal via respective electrode combinations, and each of the electrode combinations may be associated with a respective therapy program. The therapy programs may be stored as a group, such that when IMD 102 generates and delivers electrical stimulation therapy via a selected group, IMD 102 delivers electrical stimulation signal via two or more therapy programs.

In some examples, IMD 102 is configured to deliver a recharge signal (e.g., one or more recharge pulses or other waveforms), which may help balance a charge accumulation that may occur within tissue proximate the electrodes used to deliver the electrical stimulation. The recharge signal may also be referred to as a "recovery signal" or a "charge balancing signal" and may have a polarity opposite to that of the electrical stimulation signal generated and delivered by IMD 102. While recharge pulses are primarily referred to herein, in other examples, a recharge signal can have any suitable waveform.

A user, such as a clinician or patient 12, may interact with a user interface of an external programmer 104 to program IMD 102. Programming of IMD 102 may refer generally to the generation and transfer of commands, programs, or other information to control the operation of IMD 102. In this manner, IMD 102 may receive the transferred commands and programs from programmer 104 to control stimulation therapy. For example, external programmer 104 may transmit therapy programs, stimulation parameter adjustments, therapy program selections, therapy program group selections, user input, or other information to control the operation of IMD 102, e.g., by wireless telemetry or wired connection.

In some cases, external programmer 104 may be characterized as a physician or clinician programmer if it is primarily intended for use by a physician or clinician. In other cases, external programmer 104 may be characterized as a patient programmer if it is primarily intended for use by a patient. A patient programmer may be generally accessible to patient 12 and, in many cases, may be a portable device that may accompany patient 12 throughout the patient's daily routine. For example, a patient programmer may receive input from patient 12 when the patient wishes to terminate or change stimulation therapy. In general, a physician or clinician programmer may support selection and generation of programs by a clinician for use by IMD 102, whereas a patient programmer may support adjustment and selection of such programs by a patient during ordinary use. In other examples, external programmer 104 may be included, or part of, an external charging device that recharges a power source of IMD 102. In this manner, a user may program and charge IMD 102 using one device, or multiple devices.

As described herein, information may be transmitted between external programmer 104 and IMD 102. Therefore, IMD 102 and programmer 104 may communicate via wireless communication using any techniques known in the art. Examples of communication techniques may include, for example, radiofrequency (RF) telemetry and inductive coupling, but other techniques are also contemplated. In some examples, programmer 104 may include a communication head that may be placed proximate to the patient's body near the IMD 102 implant site in order to improve the quality or security of communication between IMD 102 and programmer 104. Communication between programmer 104 and IMD 102 may occur during power transmission or separate from power transmission.

In some examples, IMD 102 delivers a recharge signal after delivery of multiple pulses of an electrical stimulation signal, which may be defined by one therapy program or by multiple therapy programs. Thus, rather than charge balancing on a pulse-by-pulse basis (e.g., delivering one recharge pulse after each electrical stimulation pulse), in some examples, IMD 102 delivers one or more recharge pulses after delivery of two or more electrical stimulation pulses. In some examples, IMD 102 delivers an electrical stimulation signal to patient 12 according to multiple therapy programs by at least interleaving pulses of two or more therapy programs, the pulses having a first polarity. In some of these examples, IMD 102 may wait to deliver one or more recharge pulses until after one or more pulses of each of the therapy programs are delivered, each recharge pulse having a second polarity opposite to the first polarity. Thus, in some examples, IMD 102 may not deliver any recharge signals between therapy programs, but, rather, may withhold the delivery of one or more recharge signals until after IMD 102 delivers a plurality of pulses according to two or more therapy programs.

According to the techniques of the disclosure, IMD 102, in response to commands from external programmer 104, delivers a plurality of lower-frequency electrical stimulation therapy programs to a target tissue area of the spinal column 20 of patient 12 via electrodes (not depicted) on leads 16. By interleaving the plurality of low-frequency electrical stimulation therapy programs, IMD 102 delivers an effective higher-frequency electrical stimulation program to the target tissue area of the spinal column 20. The higher-frequency electrical stimulation program results from a combination of the lower-frequency electrical stimulation programs. In some examples, the combined program may have a frequency that is a sum of the frequencies of the lower-frequency programs. Further, the surrounding tissue of patient 12 receives only lower-frequency electrical stimulation. A lower frequency electrical stimulation programs each may define delivery of stimulation pulses at the lower frequency. The higher frequency electrical stimulation results from the combination of the lower frequency stimulation pulses.

Higher frequencies may be achieved by combining two, three, four or more sets of stimulation pulses on a time-interleaved basis. It may be desirable to expose the tissue to combined stimulation pulses at higher frequencies, e.g., with combined stimulation pulses at a frequency of greater than approximately 1.2 kHz, combined stimulation pulses at a frequency of greater than 1.5 kHz, or combined stimulation pulses at a frequency between 5 and 10 kHz. Higher-frequency stimulation may be effective in alleviating or reducing chronic pain while avoiding the need to cause paresthesia in patients. Therefore, by delivering lower-frequency stimulation at different electrode sites using multiple programs, tissues located within the electrical field of the multiple programs will be exposed, in effect, to frequencies higher than the frequencies being delivered by the individual sets of electrodes themselves. In particular, the lower frequency stimulation pulses delivered by each set of electrodes combine to the effect of a higher frequency stimulation pulses when delivered on a time-interleaved basis with one another. This allows the ability to create specific areas of high frequency therapy that are not necessarily located immediately next to the electrodes, which allows more flexibility in targeting the higher frequency to the targeted location that may not be immediately near an electrode and can reduce side effects if providing high frequency stimulation is not desired by the electrodes.

In some examples, IMD 102 is configured to generate and deliver electrical stimulation therapy to patient 12 via two or more pairs of electrodes, e.g., of leads 16 and/or a housing of IMD 102. The electrical stimulation therapy signal may have a frequency of greater than approximately 600 Hertz in some examples, greater than 1,200 Hertz in other examples, and greater than 1400 Hertz in still other examples. Additionally, the electrical stimulation therapy signal may have a frequency of less than approximately 1,500 Hertz in some examples. In some examples, the frequency may be greater than approximately 600 Hertz and less than approximately 1,500 Hertz, greater than approximately 1,200 Hertz and less than approximately 1,500 Hertz in other examples, and greater than approximately 1,200 Hertz and less than approximately 1,250 Hertz in still other examples. In some examples, the signal has a frequency of approximately 1,200 Hertz.

In some examples, the combined pulse train signal may have a frequency of greater than approximately 1,200 Hertz in some examples, greater than 1,500 Hertz in other examples, greater than 5,000 Hertz in other examples, or greater than 10,000 Hertz in still other examples. Additionally, the combined pulse train signal may have a frequency of less than approximately 20,000 Hertz in some examples, less than 10,000 Hertz in other examples, or less than 5,000 Hertz in still other examples.

In some examples, the combined pulse train signal may have a frequency greater than approximately 900 Hertz and less than approximately 1,500 Hertz. In other examples, the combined pulse train signal may have a frequency may be greater than approximately 1,200 Hertz and less than approximately 20,000 Hertz, or greater than approximately 1,200 Hertz and less than approximately 5,000 Hertz in other examples. In some examples, the signal has a frequency of approximately 4,800 Hertz. In a different example, the frequency may be greater than approximately 5,000 Hertz and less than approximately 20,000 Hertz, greater than approximately 5,000 Hertz and less than approximately 10,000 Hertz in other examples, and greater than approximately 10,000 Hertz and less than approximately 20,000 Hertz in still other examples. In some examples, the signal has a frequency of approximately 10,000 Hertz.

In some examples, the amplitude and pulse width of the electrical stimulation signal are selected such that a stimulation intensity level of the electrical stimulation signal is less than a perception or paresthesia threshold intensity level for patient 12. Stimulation delivered at an intensity that is less than a perception or paresthesia threshold intensity level for patient 12 may be referred to as sub-threshold stimulation. The perception threshold is the lowest level of electrical stimulation that is sufficient for the patient to perceive that the IMD is delivering electrical stimulation. The paresthesia threshold is the lowest level of electrical stimulation that causes paresthesia in the patient. Paresthesia may cause discomfort in the patient, and is sometimes described as a "pins and needles" sensation. A clinician may select one or more parameters of the electrical stimulation therapy, and titrate the one or more parameters until the electrical stimulation therapy is less than a perception or paresthesia threshold intensity level for patient 12. In one example, the electrical stimulation signal has a current amplitude in a range of 0.1 microamps to 100 milliamps. In another example, the amplitude may be selected to be in a range of about 0.1 milliamps to about 25 milliamps, such as in a range of about 0.5 milliamps to about 5 milliamps. In another example, the electrical stimulation signal has a voltage amplitude in a range of 10 millivolts to 14 Volts. In another example, the electrical stimulation signal has a voltage amplitude in a range of 50 millivolts to 14 Volts, such as in a range of about 500 millivolts to about 5 Volts.

In one example, the electrical stimulation signal comprises of one or more electrical pulses (e.g., a pulse train), wherein each pulse has a pulse width in a range of 2 microseconds to 833 microseconds. In a further example, each pulse has a pulse width of about 20 microseconds to about 60 microseconds. In one example, the electrical stimulation signal comprises of one or more electrical pulses (e.g., a pulse train), wherein each pulse has a pulse width in a range of 30 microseconds to 60 microseconds. In one example, the electrical stimulation signal comprises of one or more electrical pulses (e.g., a pulse train), wherein each pulse has a pulse width of approximately 50 microseconds. In one example, the electrical stimulation signal comprises of one or more electrical pulses (e.g., a pulse train), wherein each pulse has a pulse width of approximately 60 microseconds.

The perception threshold and the paresthesia threshold may differ from patient to patient. In one example, a clinician determines the intensity of the electrical stimulation by titrating the electrical stimulation therapy to determine the amplitude of the electrical stimulation required to cause one of perception of stimulation or paresthesia in the patient. In this example, the clinician selects parameters defining the electrical stimulation therapy such that the electrical stimulation therapy falls below one or both of the perception threshold or the paresthesia threshold of the patient. For example, the clinician may select an amplitude for the electrical stimulation therapy that is x % (e.g., x=60) of an amplitude that causes one or both of perception or paresthesia in the patient.

In some examples, IMD 102 delivers the pulses of the electrical stimulation signal via different electrode combinations. For example, IMD 102 may alternate delivery of pulses between two different electrode combinations, or may otherwise interleave the pulses using two or more electrode combinations in any suitable order. In some examples, IMD 102 may deliver time-interleaved pulses via two, three, four or more electrode combinations. IMD 102 may alternate between delivery of a single pulse on each of two or more electrode combinations over a series of time intervals. As an illustration, IMD 102 may deliver a first pulse in a first time interval via a first electrode combination, a second pulse in a second time interval via a second electrode combination, a third pulse in a third time interval via a third electrode combination, and a fourth pulse in a fourth time interval via a fourth electrode combination, and repeat this process, e.g., on a periodic basis. In other examples, IMD 102 may alternate between delivery of multiple pulses between two or more different electrode combinations over successive time intervals. As an illustration, IMD 102 may deliver a two or more first pulses in a first time interval via a first electrode combination, two or more second pulses in a second time interval via a second electrode combination, two or more third pulses in a third time interval via a third electrode combination, and two or more fourth pulses in a fourth time interval via a fourth electrode combination, and repeat this process, e.g., on a periodic basis. In one example, each electrode combination comprises one electrode functioning as an anode and another electrode functioning as a cathode, and these electrodes are unique to the electrode combination, i.e., the electrodes used for delivery of stimulation pulses in one electrode combinations are not used in any of the other electrode combinations. In another example, each electrode combination comprises a plurality of electrodes functioning as anodes in conjunction with a cathode and/or a plurality of electrodes functioning as cathodes in conjunction with an anode, and each of these pluralities of electrodes is unique to the electrode combination.

Regardless of the number of electrode combinations with which IMD 102 delivers the pulses, however, the combined pulse train signal may have a frequency of greater than approximately 1,200 Hertz in some examples, greater than 1,500 Hertz in other examples, greater than 5,000 Hertz in other examples, or greater than 10,000 Hertz in still other examples. In still further examples, the combined pulse train signal may have a frequency greater than approximately 900 Hertz and less than approximately 1,500 Hertz. Additionally, the combined pulse train signal may have a frequency of less than approximately 20,000 Hertz in some examples, less than 10,000 Hertz in other examples, or less than 5,000 Hertz in still other examples. In some examples, the frequency may be greater than approximately 1,200 Hertz and less than approximately 20,000 Hertz, or greater than approximately 1,200 Hertz and less than approximately 5,000 Hertz in other examples. In some examples, the signal has a frequency of approximately 4,800 Hertz. In a different example, the frequency may be greater than approximately 5,000 Hertz and less than approximately 20,000 Hertz, greater than approximately 5,000 Hertz and less than approximately 10,000 Hertz in other examples, and greater than approximately 10,000 Hertz and less than approximately 20,000 Hertz in still other examples. In some examples, the signal has a frequency of approximately 10,000 Hertz.

In another example, a clinician selects the target tissue area by selecting different electrode combinations of IMD 102 that share common anodes or cathode electrodes. For example, the clinician may select electrode combinations using electrodes proximate to each other that typically have a separation of 1 to 12 mm to deliver a combined pulse train signal to a narrow region to tissue. In another example, the clinician may select electrode combinations using electrodes far apart, such as a distance greater than 12 mm, from each other to deliver a combined pulse train signal to a wide region to tissue. For example, the clinician may select electrode combinations having a plurality of anodes around the dorsal column of patient 12, and a shared cathode in the middle of the spinal column 20 of patient 12. In this example, only the tissue proximate to the cathode electrode may receive the combined pulse train, while other tissues of patient 12 may receive only low-frequency electrical stimulation. In another example, when one or more axial leads carrying electrodes 116, 118 is placed substantially parallel to the spine 20, the clinician may select electrode combinations along the axial lead having a plurality of unique anodes located down the spine 20 and a plurality of common cathodes located in the dorsal root of patient 12. In this example, the dorsal root area may receive the combined pulse train, while other tissues of patient 12 may receive only low-frequency electrical stimulation.

In another example, a clinician selects the target tissue area by selecting different electrode combinations of IMD 102 that do not share common anodes electrodes or cathode electrodes. Such a combination may create a localized area where the cathodes of each program are near each other but do not use the same electrodes. In response to a selection by the clinician of a magnitude of an amplitude of the therapy program, different nerves or structures in and around the spinal cord of patient 12 will be exposed to the electrical field generated by pulses from one or more combinations of the selected electrodes. In other words, different nerves and associated target tissue areas on the nervous system of patient 12 may simultaneously receive electrical stimulation at different frequencies. For example, an axial lead carrying electrodes numbered sequentially 0-7 is placed substantially parallel to the spine 20. In one example, the clinician selects electrodes 0, 1 as a first electrode combination and electrodes 6, 7 as a second electrode combination. In this example, the electrode combinations are farthest apart on the axial lead. Tissue proximate to electrodes 0, 1, 6, and 7 may receive only the low-frequency electrical pulses defined by the corresponding electrical stimulation therapy program. However, in this example, a wide region of tissue may receive the combined electrical stimulation pulse train (e.g., tissue between electrode pairs 0,1 and 6,7, such as the tissue proximate to electrodes 2, 3, 4, and 5).

In another example, the clinician selects electrodes 1, 2 as a first electrode combination and electrodes 5, 6 as a second electrode combination. In this example, the electrode combinations are approximately midway along the axial lead. Tissue proximate to electrodes 1, 2, 5, and 6 may receive only the low-frequency electrical pulses defined by the corresponding electrical stimulation therapy program. However, in this example, a moderate region of tissue may receive the combined electrical stimulation pulse train (e.g., tissue between electrode pairs 1,2 and 5,6, such as the tissue proximate to electrodes 3 and 4).

In another example, the clinician selects electrodes 2, 3 as a first electrode combination and electrodes 4, 5 as a second electrode combination. In this example, the electrode combinations are closest together on the axial lead. Tissue proximate to electrodes 2, 3, 4, and 5 may receive only the low-frequency electrical pulses defined by the corresponding electrical stimulation therapy program. However, in this example, a narrow region of tissue may receive the combined electrical stimulation pulse train (e.g., tissue between electrodes 3 and 4).

Accordingly, the techniques of the disclosure allow an IMD to deliver higher frequency stimulation using interleaved low-frequency electrical stimulation therapy programs. Such an IMD may provide stimulation at higher rates more effectively than other devices because the tissue near each of the electrodes receive lower frequency stimulation, and thereby less energy, while the targeted tissue area receives the effective high-frequency stimulation. Furthermore, an IMD according to the techniques of the disclosure may allow for a clinician to more precisely apply stimulation at varying frequencies to different tissues in a manner that may not be possible with some other IMDs that deliver only a single high-frequency electrical stimulation program over a pair of electrodes.

Although IMD 102 is generally described herein, techniques of this disclosure may also be applicable to external or partially external medical device in other examples. For example, IMD 102 may instead be configured as an external medical device coupled to one or more percutaneous medical leads. The external medical device may be a chronic, temporary, or trial electrical stimulator. In addition, an external electrical stimulator may be used in addition to one or more IMDs 102 to deliver electrical stimulation described herein.

Figure 2:
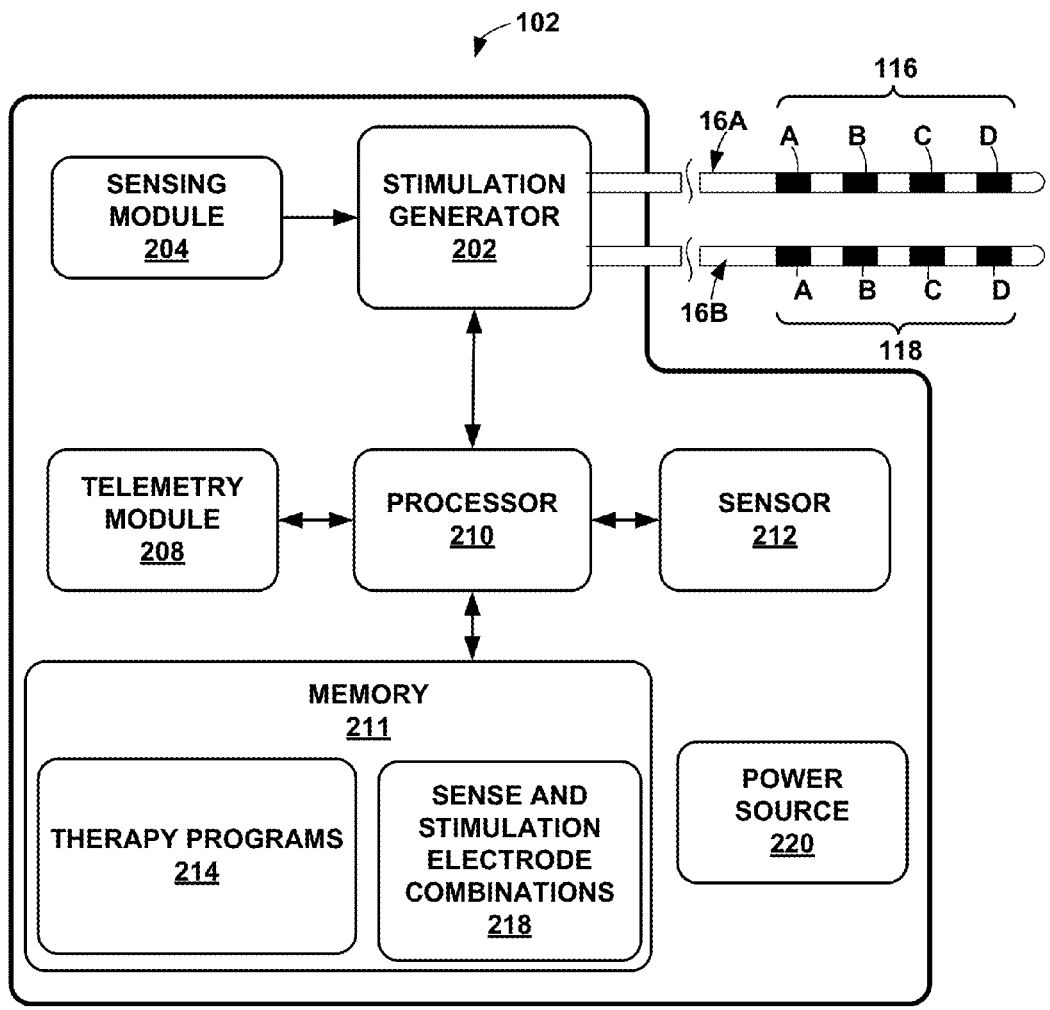
FIG. 2 is a block diagram of the example IMD of FIG. 1.

FIG. 2 is a block diagram of the example IMD 102 of FIG. 1. In the example shown in FIG. 2, IMD 102 includes processor 210, memory 211, stimulation generator 202, sensing module 204, telemetry module 208, sensor 212, and power source 220. Each of these modules may be or include electrical circuitry configured to perform the functions attributed to each respective module. For example, processor 210 may include processing circuitry, stimulation generator 202 may include switch circuitry, sensing module 204 may include sensing circuitry, and telemetry module 208 may include telemetry circuitry. Memory 211 may include any volatile or non-volatile media, such as a random access memory (RAM), read only memory (ROM), non-volatile RAM (NVRAM), electrically erasable programmable ROM (EEPROM), flash memory, and the like. Memory 211 may store computer-readable instructions that, when executed by processor 210, cause IMD 102 to perform various functions. Memory 211 may be a storage device or other non-transitory medium.

In the example shown in FIG. 2, memory 211 stores therapy programs 214 and sense electrode combinations and associated stimulation electrode combinations 218 in separate memories within memory 211 or separate areas within memory 211. Each stored therapy program 214 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group include stimulation pulses that may be delivered together on an overlapping or non-overlapping (e.g., time-interleaved) basis.

The techniques of the disclosure are described as interleaving stimulation pulses on a non-overlapping (time-interleaved) basis. However, in some examples, the techniques of the disclosure may allow for interleaving stimulation pulses delivered via different sets of electrodes on an at least partially overlapping basis. Overlapping of the recharge or recovery pulses of the different programs or electrode combinations may be useful because it may allow more time to discharge series capacitors on the electrodes. This may allow the system to operate more efficiently. For example, each of the plurality of electrical stimulation programs delivers therapy pulses on unique electrodes. However, during the time of the recovery pulse, each of the electrodes used in all of the electrical stimulation therapy programs are tied together on the IMD and connected to the body. This allows the series capacitors of the electrodes to simultaneously discharge to balance the therapy pulses. Such a system allows for recovery pulses having a lower amplitude than other systems, and therefore, such a system may disperse the energy more uniformly to the tissue of the patient instead of localizing it to the specific electrode combination.

Accordingly, in some examples, stimulation generator 202 generates electrical stimulation signals in accordance with the electrical stimulation parameters noted above. Other ranges of therapy parameter values may also be useful, and may depend on the target stimulation site within patient 112. While stimulation pulses are described, stimulation signals may be of any form, such as continuous-time signals (e.g., sine waves) or the like.

Processor 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 210 herein may be embodied as firmware, hardware, software or any combination thereof. Processor 210 controls stimulation generator 202 according to therapy programs 214 stored in memory 211 to apply particular stimulation parameter values specified by one or more of programs, such as amplitude, pulse width, and pulse rate.

In the example shown in FIG. 2, the set of electrodes 116 includes electrodes 116A, 116B, 116C, and 116D, and the set of electrodes 118 includes electrodes 118A, 118B, 118C, and 118D. Processor 210 also controls stimulation generator 202 to generate and apply the stimulation signals to selected combinations of electrodes 116, 118. In some examples, stimulation generator 202 includes a switch module that couples stimulation signals to selected conductors within leads 16, which, in turn, deliver the stimulation signals across selected electrodes 116, 118. Such a switch module may be a switch array, switch matrix, multiplexer, or any other type of switching module configured to selectively couple stimulation energy to selected electrodes 116, 118 and to selectively sense bioelectrical neural signals of spine 20 with selected electrodes 116, 118.

In other examples, however, stimulation generator 202 does not include a switch module. In these examples, stimulation generator 202 comprises a plurality of pairs of voltage sources, current sources, voltage sinks, or current sinks connected to each of electrodes 116, 118 such that each pair of electrodes has a unique signal generator. In other words, in these examples, each of electrodes 116, 118 is independently controlled via its own signal generator (e.g., via a combination of a regulated voltage source and sink or regulated current source and sink), as opposed to switching signals between electrodes 116, 118.

Stimulation generator 202 may be a single channel or multi-channel stimulation generator. In particular, stimulation generator 202 may be capable of delivering a single stimulation pulse or multiple stimulation pulses at a given time via a single electrode combination or multiple stimulation pulses at a given time via multiple electrode combinations. In some examples, however, stimulation generator 202 may be configured to deliver multiple channels on a time-interleaved basis. For example, a switch module of stimulation generator 202 may serve to time divide the output of stimulation generator 202 across different electrode combinations at different times to deliver multiple programs or channels of stimulation energy to patient 112. In another example, the stimulation generator 202 may control the independent sources or sinks on a time-interleaved bases.

Electrodes 116, 118 on respective leads 16 may be constructed of a variety of different designs. For example, one or both of leads 16 may include two or more electrodes at each longitudinal location along the length of the lead, such as multiple electrodes at different perimeter locations around the perimeter of the lead at each of the locations A, B, C, and D. On one example, the electrodes may be electrically coupled to switch module 206 via respective wires that are straight or coiled within the housing the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 16. These and other constructions may be used to create a lead with a complex electrode geometry.

Although sensing module 204 is incorporated into a common housing with stimulation generator 202 and processor 210 in FIG. 2, in other examples, sensing module 204 may be in a separate housing from IMD 102 and may communicate with processor 210 via wired or wireless communication techniques. Example bioelectrical signals include, but are not limited to, a signal generated from local field potentials within one or more regions of spine 20.

Sensor 212 may include one or more sensing elements that sense values of a respective patient parameter. For example, sensor 212 may include one or more accelerometers, optical sensors, chemical sensors, temperature sensors, pressure sensors, or any other types of sensors. Sensor 212 may output patient parameter values that may be used as feedback to control delivery of therapy. IMD 102 may include additional sensors within the housing of IMD 102 and/or coupled via one of leads 16 or other leads. In addition, IMD 102 may receive sensor signals wirelessly from remote sensors via telemetry module 208, for example. In some examples, one or more of these remote sensors may be external to patient (e.g., carried on the external surface of the skin, attached to clothing, or otherwise positioned external to the patient).

Telemetry module 208 supports wireless communication between IMD 102 and an external programmer 104 or another computing device under the control of processor 210. Processor 210 of IMD 102 may receive, as updates to programs, values for various stimulation parameters such as amplitude and electrode combination, from programmer 104 via telemetry module 208. The updates to the therapy programs may be stored within therapy programs 214 portion of memory 211. Telemetry module 208 in IMD 102, as well as telemetry modules in other devices and systems described herein, such as programmer 104, may accomplish communication by radiofrequency (RF) communication techniques. In addition, telemetry module 208 may communicate with external medical device programmer 104 via proximal inductive interaction of IMD 102 with programmer 104. Accordingly, telemetry module 208 may send information to external programmer 104 on a continuous basis, at periodic intervals, or upon request from IMD 102 or programmer 104.

Power source 220 delivers operating power to various components of IMD 102. Power source 220 may include a small rechargeable or non-rechargeable battery and a power generation circuit to produce the operating power. Recharging may be accomplished through proximal inductive interaction between an external charger and an inductive charging coil within IMD 220. In some examples, power requirements may be small enough to allow IMD 220 to utilize patient motion and implement a kinetic energy-scavenging device to trickle charge a rechargeable battery. In other examples, traditional batteries may be used for a limited period of time.

According to the techniques of the disclosure, telemetry module 208 of IMD 102 receives commands from an external programmer 104. In response to these commands, processor 210 of IMD 102 delivers a plurality of low-frequency electrical stimulation therapy programs to a target tissue area of the spinal column 20 of patient 12 via electrodes 116, 118 of leads 16. By interleaving the plurality of low-frequency electrical stimulation therapy programs delivered by each of electrodes 116, 118, IMD 102 delivers to the target tissue area a combined pulse train that is effectively a high-frequency pulse train.

In some examples, IMD 102 is configured to generate and deliver electrical stimulation therapy to patient 12 via two or more pairs of electrodes, e.g., combinations of two or more of electrodes 116A-116D and 118A-118D, e.g., of leads 16 and/or a housing of IMD 102. In some examples, each individual pulse train delivered on the two or more pairs of electrodes has a frequency in a range of about 600 Hertz to about 1500 Hertz. The amplitude and pulse width of the electrical stimulation signal are selected such that a stimulation intensity level of the electrical stimulation signal is less than a perception or paresthesia threshold intensity level for patient 12. For example, in a current-controlled implementation, the amplitude may be selected to be in a range of 0.1 microamps to 100 milliamps. In another example, the amplitude may be selected to be in a range of about 0.1 milliamps to about 25 milliamps, such as in a range of about 0.5 milliamps to about 5 milliamps. In another example, in a voltage-controlled implementation, the amplitude may be selected to be in a range of 10 millivolts to 14 Volts. In another example, the voltage amplitude may be selected to be in a range of about 50 millivolts to about 14 volts, such as in a range of about 500 millivolts to about 5 Volts.

In one example, the electrical stimulation signal comprises of one or more electrical pulses (e.g., a pulse train), wherein each pulse has a pulse width in a range of 2 microseconds to 833 microseconds. In a further example, each pulse has a pulse width of about 20 microseconds to about 60 microseconds. In one example, the electrical stimulation signal comprises of one or more electrical pulses (e.g., a pulse train), wherein each pulse has a pulse width in a range of 30 microseconds to 60 microseconds. In one example, the electrical stimulation signal comprises of one or more electrical pulses (e.g., a pulse train), wherein each pulse has a pulse width of approximately 50 microseconds. In one example, the electrical stimulation signal comprises of one or more electrical pulses (e.g., a pulse train), wherein each pulse has a pulse width of approximately 60 microseconds.

In some examples, IMD 102 delivers the pulses of the electrical stimulation signal via different electrode combinations of two or more of electrodes 116A-116D and 118A-118D and a housing of IMD 102. For example, IMD 102 may alternate delivery of pulses between two or more different electrode combinations, or may otherwise interleave the pulses using two or more electrode combinations in any suitable order. In one example, each electrode combination comprises at least one electrode functioning as an anode and at least one other electrode functioning as a cathode, and these electrodes are unique to the electrode combination in that the same electrodes are not used in other electrode combinations that are used to delivery time-interleaved stimulation pulses.

The electrical stimulation therapy signal may have a frequency of greater than approximately 600 Hertz in some examples, greater than 1,200 Hertz in other examples, and greater than 1400 Hertz in still other examples. Additionally, the electrical stimulation therapy signal may have a frequency of less than approximately 1,500 Hertz in some examples. In some examples, the frequency may be greater than approximately 600 Hertz and less than approximately 1,500 Hertz, greater than approximately 1,200 Hertz and less than approximately 1,500 Hertz in other examples, and greater than approximately 1,200 Hertz and less than approximately 1,250 Hertz in still other examples. In some examples, the signal has a frequency of approximately 1,200 Hertz.

The combined pulse train signal may have a frequency of greater than approximately 1,200 Hertz in some examples, greater than 1,500 Hertz in other examples, greater than 5,000 Hertz in other examples, or greater than 10,000 Hertz in still other examples. Additionally, the combined pulse train signal may have a frequency of less than approximately 20,000 Hertz in some examples, less than 10,000 Hertz in other examples, or less than 5,000 Hertz in still other examples. In some examples, the frequency may be greater than approximately 1,200 Hertz and less than approximately 20,000 Hertz, or greater than approximately 1,200 Hertz and less than approximately 5,000 Hertz in other examples. In some examples, the signal has a frequency of approximately 4,800 Hertz. In a different example, the frequency may be greater than approximately 5,000 Hertz and less than approximately 20,000 Hertz, greater than approximately 5,000 Hertz and less than approximately 10,000 Hertz in other examples, and greater than approximately 10,000 Hertz and less than approximately 20,000 Hertz in still other examples. In some examples, the signal has a frequency of approximately 10,000 Hertz.

In another example, in response to telemetry module 208 receiving commands from an external programmer 104, processor 210 of IMD 102 selects the target tissue area by selecting different electrode combinations of two or more of electrodes 116A-116D and 118A-118D and a housing of IMD 102 that share common anodes electrodes or cathode electrodes. For example, processor 210 of IMD 102 selects a first combination having anode electrode 116A and cathode electrode 118A, a second combination having anode electrode 116B and cathode electrode 118A, a third having anode electrode 116C and cathode electrode 118A, and a fourth combination having anode electrode 116D and cathode electrode 118A. In this example, only the tissue proximate to the cathode electrode 118A may receive the combined pulse train signal, while other tissues of patient 12 near anode electrodes 116A-116D may receive only low-frequency electrical stimulation.

In another example, in response to telemetry module 208 receiving commands from an external programmer 104, processor 210 of IMD 102 selects the target tissue area by selecting electrode combinations having a plurality of unique anodes located down the spine 20 and a plurality of common cathodes located in the dorsal root of patient 12. In this example, processor 210 of IMD 102 selects a first combination having anode electrode 116A and cathode electrodes 118A-118D, a second combination having anode electrode 116B and cathode electrodes 118A-118D, a third combination having anode electrode 116C and cathode electrodes 118A-118D, and a fourth combination having anode electrode 116D and cathode electrodes 118A-118D. In this example, the dorsal root area of patient 12 (e.g., the tissue near cathode electrodes 118A-118D) may receive the combined pulse train, while other tissues of patient 12 (e.g., the tissue near anode electrodes 116A-116D) may receive only low-frequency electrical stimulation.

In another example, in response to telemetry module 208 receiving commands from an external programmer 104, processor 210 of IMD 102 selects the target tissue area by selecting different electrode combinations of two or more of electrodes 116A-116D and 118A-118D and a housing of IMD 102 that do not share common anodes electrodes or cathode electrodes. Such a combination may create a localized area where the cathodes of each program are near each other but do not use the same electrodes. For example, in response to receiving a selection of a magnitude of an amplitude of the therapy program, processor 210 of IMD 102 delivers electrical therapy to different nerves of patient 12 such that different nerves and associated target tissue areas on the nervous system of patient 12 may simultaneously receive electrical stimulation at different frequencies. For example, processor 210 of IMD 102 selects a first combination having anode electrode 116A and cathode electrode 118A, a second combination having anode electrode 116B and cathode electrode 118B, a third combination having anode electrode 116C and cathode electrode 118C, and a fourth combination having anode electrode 116D and cathode electrode 118D. In this example, tissue between the combinations of electrodes may receive the combined pulse train, while other tissues of patient 12 (e.g., tissues not proximate to the electrodes) may receive only low-frequency electrical stimulation.

In some examples, processor 210 selects combinations of electrodes such that the space between the anode and cathode for each program is increased, thus increasing the spread of the stimulation and increasing the likelihood of the same target area being affected by multiple programs. In other examples, processor 210 selects combinations of electrodes such that the space between the anode and cathode for each program is decreased, thus decreasing the spread of the stimulation and increasing the likelihood of the same target area being affected by multiple programs.

Accordingly, the techniques of the disclosure allow an IMD 102 to deliver higher frequency stimulation using interleaved low-frequency electrical stimulation therapy programs. Such an IMD 102 may provide stimulation at higher rates more effectively than other devices because the tissue near each of the electrodes receive lower frequency stimulation, and thereby less energy, while the targeted tissue area receives the effective high-frequency stimulation. Furthermore, such an IMD 102 uses proven technology that has already been developed. Therefore, an IMD 102 according to the techniques of the disclosure allows for a clinician to more precisely apply stimulation at varying frequencies to different tissues in a manner not possible with other IMDs that deliver only a single high-frequency electrical stimulation program over a pair of electrodes.

The architecture of IMD 102 illustrated in FIG. 2 is shown as an example. The techniques as set forth in this disclosure may be implemented in the example IMD 102 of FIG. 2, as well as other types of systems not described specifically herein. Nothing in this disclosure should be construed so as to limit the techniques of this disclosure to the example architecture illustrated by FIG. 2.

Figure 3:
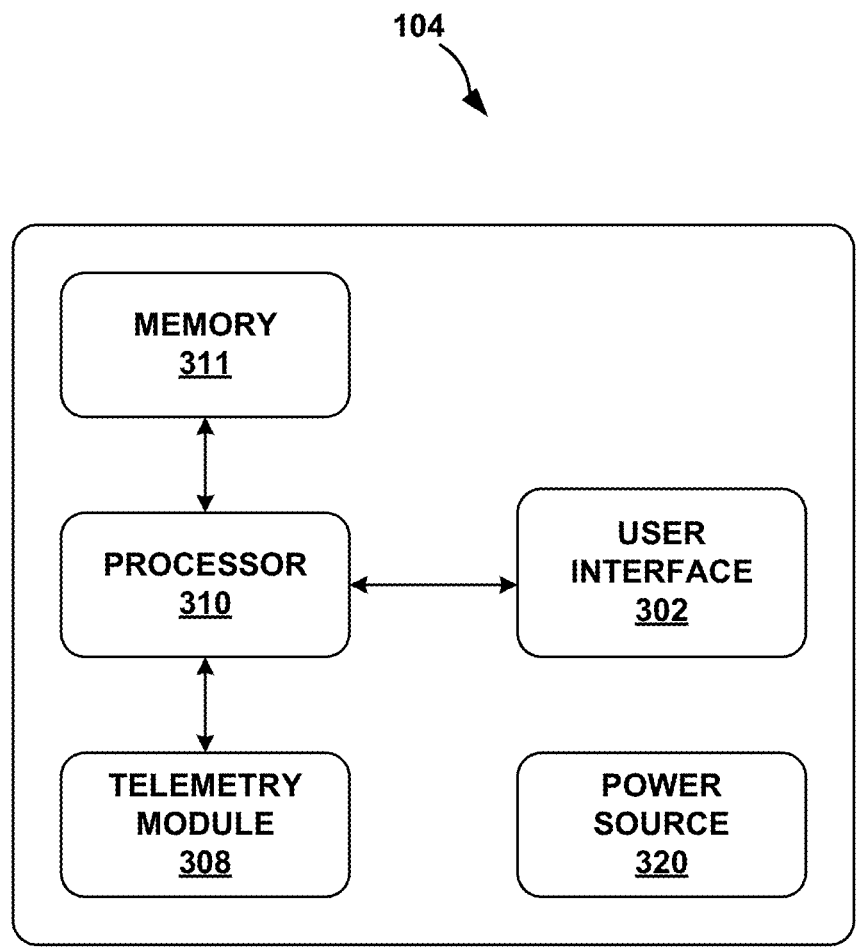
FIG. 3 is a block diagram of the example external programmer of FIG. 1.

FIG. 3 is a block diagram of the example external programmer 104 of FIG. 1. Although programmer 104 may generally be described as a hand-held device, programmer 104 may be a larger portable device or a more stationary device. In addition, in other examples, programmer 104 may be included as part of an external charging device or include the functionality of an external charging device. As illustrated in FIG. 3, programmer 104 may include a processor 310, memory 311, user interface 302, telemetry module 308, and power source 320. Memory 311 may store instructions that, when executed by processor 310, cause processor 310 and external programmer 104 to provide the functionality ascribed to external programmer 104 throughout this disclosure. Each of these components, or modules, may include electrical circuitry that is configured to perform some or all of the functionality described herein. For example, processor 310 may include processing circuitry configured to perform the processes discussed with respect to processor 310.

In general, programmer 104 comprises any suitable arrangement of hardware, alone or in combination with software and/or firmware, to perform the techniques attributed to programmer 104, and processor 310, user interface 302, and telemetry module 308 of programmer 104. In various examples, programmer 104 may include one or more processors, such as one or more microprocessors, DSPs, ASICs, FPGAs, or any other equivalent integrated or discrete logic circuitry, as well as any combinations of such components. Programmer 104 also, in various examples, may include a memory 311, such as RAM, ROM, PROM, EPROM, EEPROM, flash memory, a hard disk, a CD-ROM, comprising executable instructions for causing the one or more processors to perform the actions attributed to them. Moreover, although processor 310 and telemetry module 308 are described as separate modules, in some examples, processor 310 and telemetry module 308 are functionally integrated. In some examples, processor 310 and telemetry module 308 correspond to individual hardware units, such as ASICs, DSPs, FPGAs, or other hardware units.

Memory 311 (e.g., a storage device) may store instructions that, when executed by processor 310, cause processor 310 and programmer 104 to provide the functionality ascribed to programmer 104 throughout this disclosure. For example, memory 311 may include instructions that cause processor 310 to obtain a parameter set from memory, select a spatial electrode movement pattern, or receive a user input and send a corresponding command to IMD 104, or instructions for any other functionality. In addition, memory 311 may include a plurality of programs, where each program includes a parameter set that defines stimulation therapy.

User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen. The input may request starting or stopping electrical stimulation, the input may request a new spatial electrode movement pattern or a change to an existing spatial electrode movement pattern, of the input may request some other change to the delivery of electrical stimulation.

Processor 310 may also control user interface 302 to display information related to an anatomical atlas (e.g., an atlas of a reference anatomy) and patient-specific anatomy. For example, user interface 302 may display a representation of one or more atlas-defined anatomical structures over a representation (e.g., an image) of the specific patient anatomy. User interface 302 may present annotation tools for adjusting the structures of the atlas to the patient anatomy and receive user annotations indicating where the corresponding structures of the patient anatomy are located and/or where the atlas should be moved with respect to the patient anatomy. Processor 310 may then adjust the position and/or size of the structures of the atlas to more closely match (e.g., a best fit) to the user annotation. After the atlas has been adjusted, the user may refer to the atlas for locations of certain structures of the patient instead of needing to continually find desired structures based on the image of the patient anatomy.

Telemetry module 308 may support wireless communication between IMD 102 and programmer 104 under the control of processor 310. Telemetry module 308 may also be configured to communicate with another computing device via wireless communication techniques, or direct communication through a wired connection. In some examples, telemetry module 308 provides wireless communication via an RF or proximal inductive medium. In some examples, telemetry module 308 includes an antenna, which may take on a variety of forms, such as an internal or external antenna.

Examples of local wireless communication techniques that may be employed to facilitate communication between programmer 104 and IMD 102 include RF communication according to the 802.11 or Bluetooth specification sets or other standard or proprietary telemetry protocols. In this manner, other external devices may be capable of communicating with programmer 104 without needing to establish a secure wireless connection. As described herein, telemetry module 308 may be configured to transmit a spatial electrode movement pattern or other stimulation parameter values to IMD 102 for delivery of stimulation therapy.

In some examples, selection of therapy parameters or therapy programs may be transmitted to a medical device (e.g., IMD 102) for delivery to patient 112. In other examples, the therapy may include medication, activities, or other instructions that patient 112 must perform themselves or a caregiver perform for patient 112. In some examples, programmer 104 may provide visual, audible, and/or tactile notifications that indicate there are new instructions. Programmer 104 may require receiving user input acknowledging that the instructions have been completed in some examples.

According to the techniques of the disclosure, user interface 302 of external programmer 104 receives a selection from a clinician of one or more combinations of electrodes for delivery of a plurality of low-frequency electrical stimulation therapies to patient 12. In response to the selection, processor 310, via telemetry module 308, issues instructions to IMD 102 to deliver the plurality of low-frequency electrical stimulation therapies. In response to the instructions, IMD 102 delivers to the target tissue area a combined pulse train that is effectively a high-frequency electrical stimulation program. In some examples, user interface 302 allows for a clinician to select one or more combinations of anode and cathode electrodes for the delivery of each electrical stimulation therapy. In other examples, user interface 302 allows for a clinician to select a high-frequency stimulation program including a desired target tissue area and desired effective frequency, and processor 310 automatically determines the appropriate combination of anode and cathode electrodes in multiple electrode combinations of IMD 102 to achieve the selected stimulation program. In this example, processor 310, via telemetry module 308, issues instructions to IMD 102 causing IMD 102 to select the appropriate combination of anode and cathode electrodes and deliver a plurality of interleaved, low-frequency electrical stimulation therapies so as to effect the selected high-frequency stimulation program, as described above.

The architecture of programmer 104 illustrated in FIG. 3 is shown as an example. The techniques as set forth in this disclosure may be implemented in the example programmer 104 of FIG. 3, as well as other types of systems not described specifically herein. Nothing in this disclosure should be construed so as to limit the techniques of this disclosure to the example architecture illustrated by FIG. 3.

Figure 4:
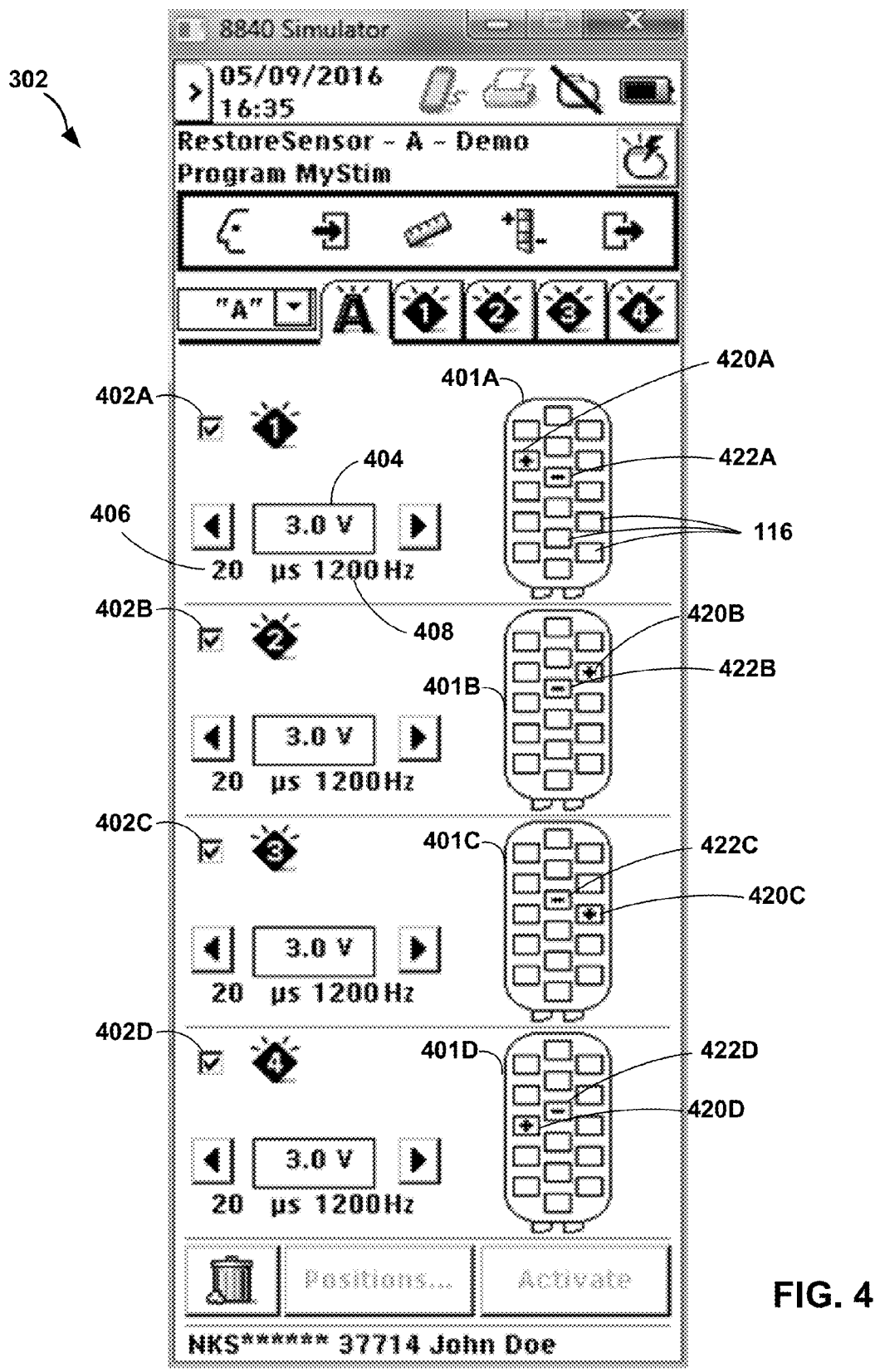
FIG. 4 is an illustration depicting an example user interface for an external programmer of FIG. 1.

FIG. 4 is an illustration depicting an example user interface 302 for an external programmer 104 of FIG. 1. In the example of FIG. 4, user interface 302 provides an interface, such as a touchscreen interface, for receiving commands from a clinician to selectively control parameters of a first, second, third, and fourth electrical stimulation therapy program.

User interface 302 provides representations 401A-401D (collectively, "representations 401") of a paddle electrode of IMD 102 of FIG. 1. Each of representation 401 of the paddle electrode displays a plurality of electrodes 116 and the configuration of each of the plurality of electrodes 116 for a respective first, second, third, and fourth electrical stimulation therapy program, which may be associated with first, second, third and fourth electrode combinations, respectively. In response to commands from a clinician, external programmer 104 may configure one or more of electrodes 116 to function as anodic or cathodic electrodes for a particular electrical stimulation therapy program. In the example of FIG. 4, user interface 302 of external programmer 104 displays electrode 420A as an anodic electrode and electrode 422A as a cathodic electrode for the first stimulation program. Further, user interface 302 of external programmer 104 displays electrode 420B as an anodic electrode and electrode 422B as a cathodic electrode for the second stimulation program. Further, user interface 302 of external programmer 104 displays electrode 420C as an anodic electrode and electrode 422C as a cathodic electrode for the third stimulation program. Further, user interface 302 of external programmer 104 displays electrode 420D as an anodic electrode and electrode 422D as a cathodic electrode for the fourth stimulation program. As illustrated in FIG. 4, each of the anodic electrodes 420A-420D and cathodic electrodes 422A-422D are different electrodes and unique to the stimulation program.

While in the example of FIG. 4, an eight-electrode system that provides for four simultaneous electrical stimulation programs is described. However, other systems may have any number of configurable electrodes and programs. As one example, a 16-electrode system allows from one to eight programs to run simultaneously on unique pairs of electrodes. Further, such a system may allow 16 programs to run simultaneously, wherein the case or housing of the IMD functions as an anode. As a further example, a 32-electrode system allows from one to 16 programs to run simultaneously on unique pairs of electrodes. Further, such a system may allow 32 programs to run simultaneously, wherein the case or housing of the IMD functions as the anode.

User interface 302 provides selection buttons 402A-402D for receiving a command from a clinician to enable or disable a respective first, second, third, and fourth electrical stimulation therapy program for delivering electrical stimulation pulses to patient 12. User interface 302 further provides a selection box 404 for receiving a command from a clinician causing external programmer 104 to adjust the amplitude of the respective electrical stimulation therapy program. In the example of FIG. 4, selection box 404 controls a voltage amplitude. However, in other examples, selection box 404 controls a current amplitude. User interface 302 further provides a pulse width indicator 406 for displaying the pulse width of electrical pulses of the respective electrical stimulation therapy program and a frequency indicator 408 for displaying the frequency of electrical pulses of the respective electrical stimulation therapy program. In some examples, user interface 404 provides means to adjust the pulse width and frequency of electrical pulses of the respective electrical stimulation therapy program.

Accordingly, the techniques of the disclosure allow an external programmer 104 to instruct an IMD 102 to deliver higher frequency stimulation using interleaved low-frequency electrical stimulation therapy programs. By combining the time-interleaved, low-frequency electrical stimulation therapy programs, such an IMD 102 may effectively provide stimulation at higher frequencies to target tissue, while tissue near each of the electrodes selected for each program receive lower frequency stimulation, and thereby less energy.

Figure 5:
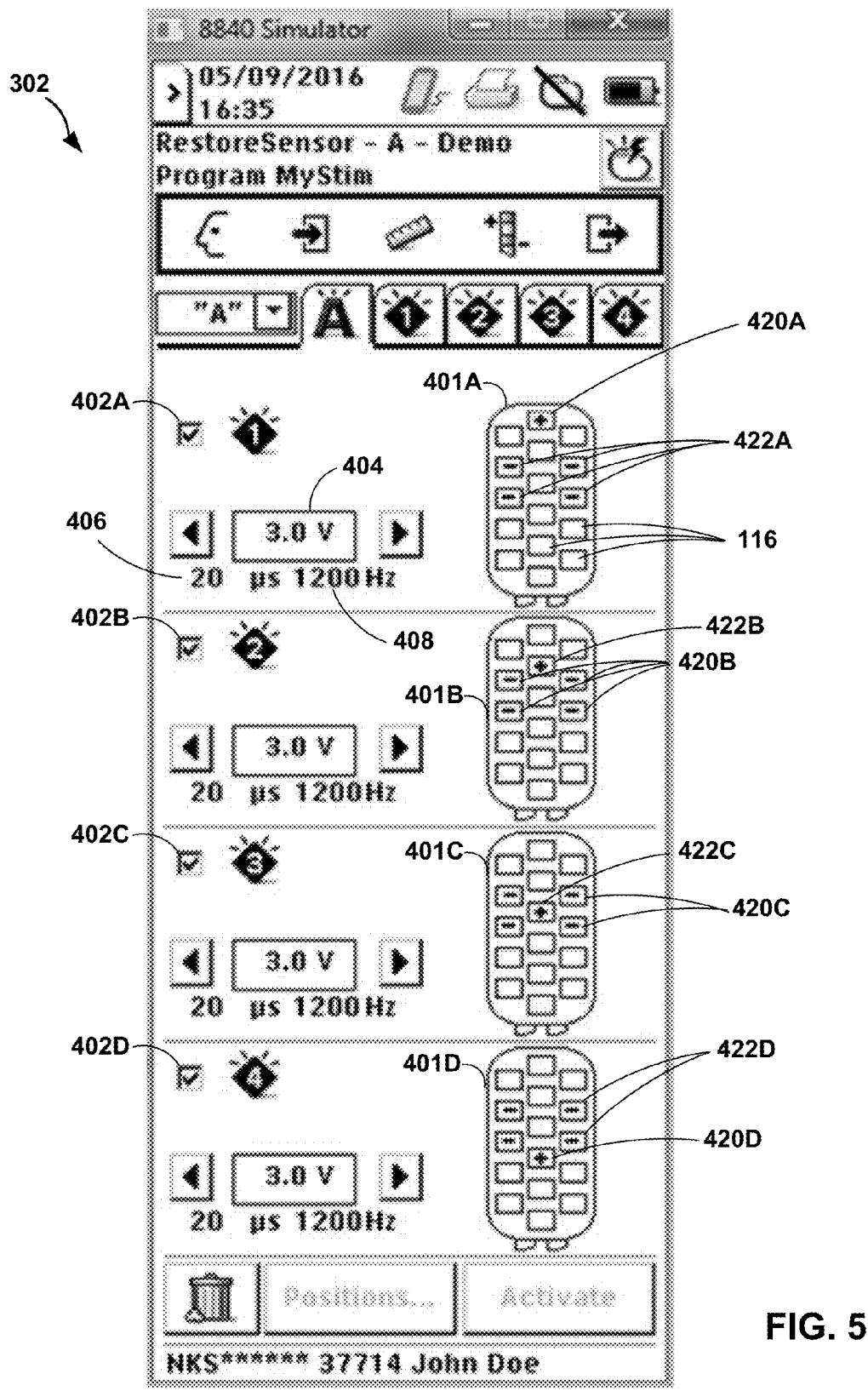
FIG. 5 is an illustration depicting an example user interface for an external programmer of FIG. 1.

FIG. 5 is an illustration depicting an example user interface 302 for an external programmer 104 of FIG. 1. The user interface 302 of FIG. 5 functions in a substantially similar fashion to the user interface 302 of FIG. 4.

In the example of FIG. 5, user interface 302 provides representations 401A-401D (collectively, "representations 401") of a paddle electrode of IMD 102 of FIG. 1. Each of representation 401 of the paddle electrode displays a plurality of electrodes 116 and the configuration of each of the plurality of electrodes 116 for a respective first, second, third, and fourth electrical stimulation therapy program. In response to commands from a clinician, external programmer 104 may configure one or more of electrodes 116 to function as anodic or cathodic electrodes for a particular electrical stimulation therapy program. In the example of FIG. 5, user interface 302 of external programmer 104 displays electrode 420A as an anodic electrode and electrodes 422A as cathodic electrodes for the first stimulation program. Further, user interface 302 of external programmer 104 displays electrode 420B as an anodic electrode and electrodes 422B as cathodic electrodes for the second stimulation program. Further, user interface 302 of external programmer 104 displays electrode 420C as an anodic electrode and electrodes 422C as cathodic electrodes for the third stimulation program. Further, user interface 302 of external programmer 104 displays electrode 420D as an anodic electrode and electrodes 422D as cathodic electrodes for the fourth stimulation program. As illustrated in FIG. 5, each of the anodic electrodes 420A-420D are different electrodes and unique to the stimulation program, while cathodic electrodes 422A-422D are the same electrodes for each stimulation program.

Accordingly, the techniques of the disclosure allow an external programmer 104 to instruct an IMD 102 to deliver higher frequency stimulation using interleaved low-frequency electrical stimulation therapy programs. By combining the time-interleaved, low-frequency electrical stimulation therapy programs, such an IMD 102 may effectively provide stimulation at higher frequencies to target tissue, while tissue near each the electrodes selected for each program receive lower frequency stimulation, and thereby less energy.

Figure 6:
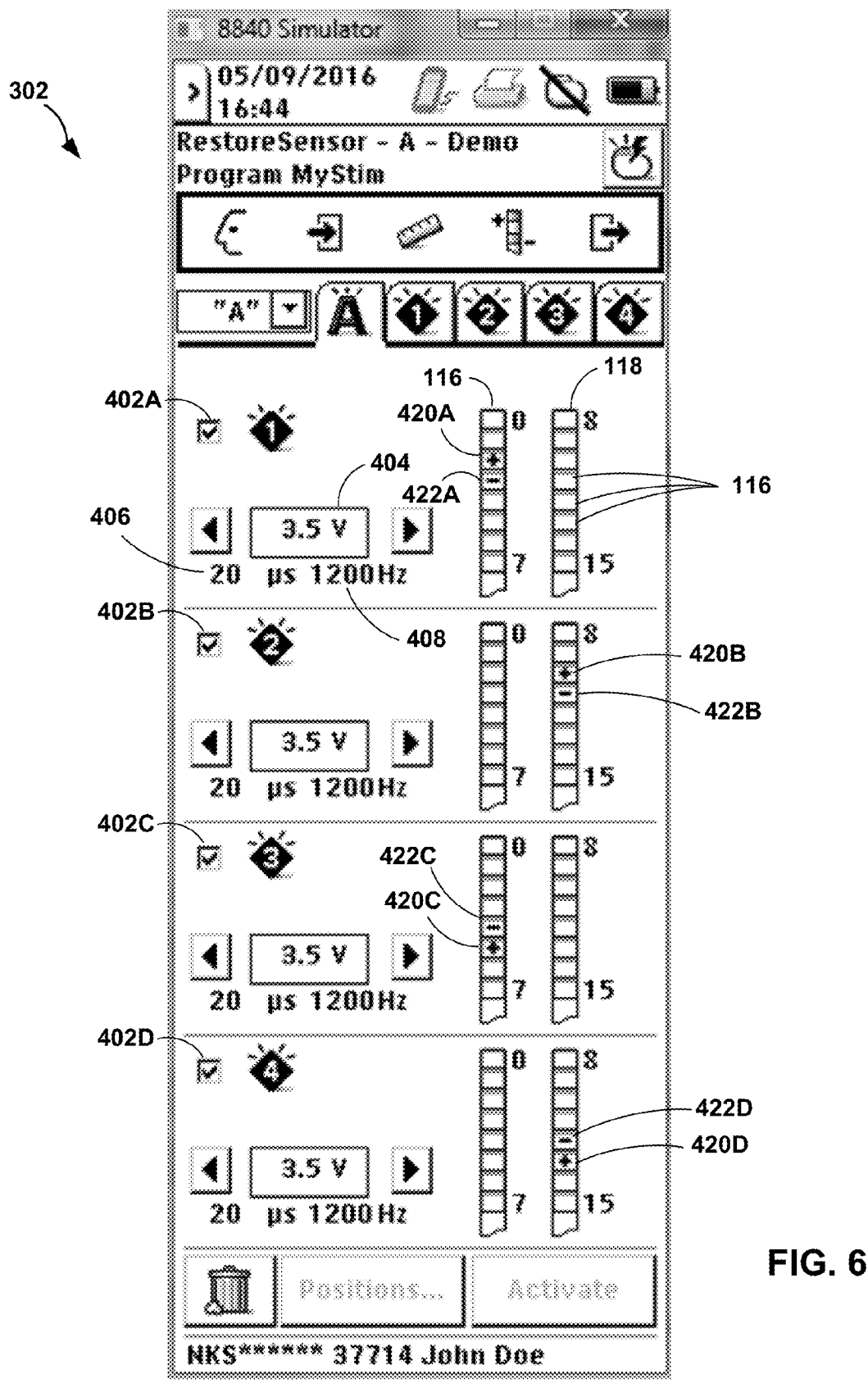
FIG. 6 is an illustration depicting an example user interface for an external programmer of FIG. 1.

FIG. 6 is an illustration depicting an example user interface for an external programmer 104 of FIG. 1. The user interface 302 of FIG. 6 functions in a substantially similar fashion to the user interface 302 of FIG. 4.

User interface 302 of FIG. 6 provides representations of electrodes 116, 118 of IMD 102 of FIG. 2 carried on axial leads. Each representation of electrodes 116, 118 displays a plurality of electrodes 116 and the configuration of each of the plurality of electrodes 116 for a respective first, second, third, and fourth electrical stimulation therapy program. In response to commands from a clinician, external programmer 104 may configure one or more of electrodes 116 to function as anodic or cathodic electrodes for a particular electrical stimulation therapy program. In the example of FIG. 6, user interface 302 of external programmer 104 displays electrode 420A as an anodic electrode and electrode 422A as a cathodic electrode for the first stimulation program. Further, user interface 302 of external programmer 104 displays electrode 420B as an anodic electrode and electrode 422B as a cathodic electrode for the second stimulation program. Further, user interface 302 of external programmer 104 displays electrode 420C as an anodic electrode and electrode 422C as a cathodic electrode for the third stimulation program. Further, user interface 302 of external programmer 104 displays electrode 420D as an anodic electrode and electrode 422D as a cathodic electrode for the fourth stimulation program. As illustrated in FIG. 4, each of the anodic electrodes 420A-420D and cathodic electrodes 422A-422D are different electrodes and unique to the stimulation program.

Figure 7A:
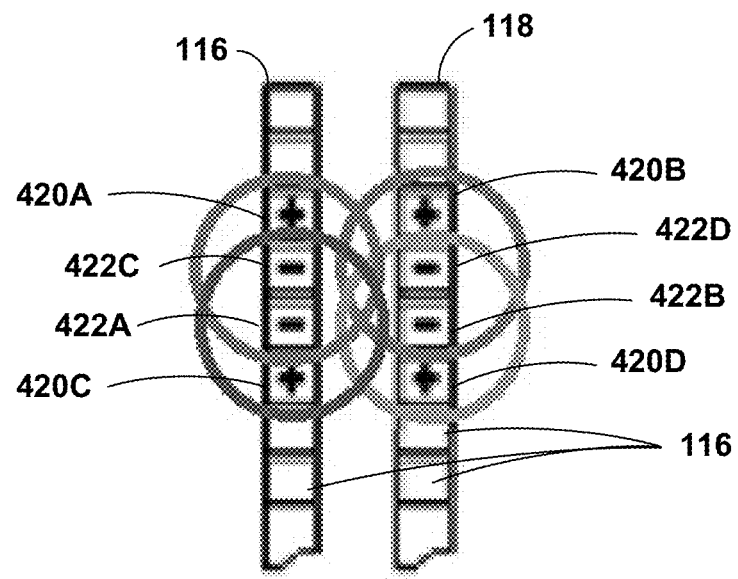
FIGS. 7A-7B are illustrations depicting example electrode leads of the IMD of FIG. 1.
Figure 7B:
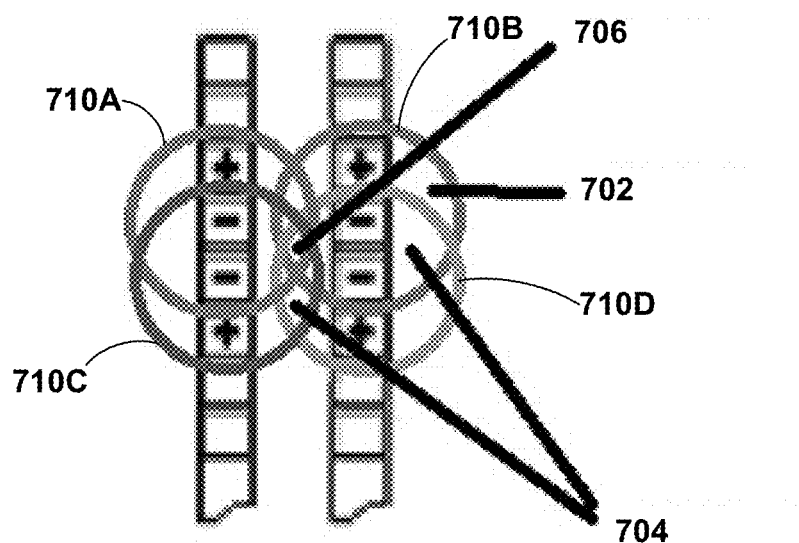

FIGS. 7A-7B are illustrations depicting example electrode leads of the IMD of FIG. 1. In the example of FIGS. 7A-7B, electrodes 116, 118 are configured in a substantially similar fashion to the electrodes depicted by user interface 302 of FIG. 6. For example, electrode 420A is configured as an anodic electrode and electrode 422A as a cathodic electrode for the first stimulation program. Further, user interface 302 of external programmer 104 displays electrode 420B as an anodic electrode and electrode 422B is configured as a cathodic electrode for the second stimulation program. Further, electrode 420C is configured as an anodic electrode and electrode 422C is configured as a cathodic electrode for the third stimulation program. Further, electrode 420D is configured as an anodic electrode and electrode 422D is configured as a cathodic electrode for the fourth stimulation program. As illustrated in FIG. 4, each of the anodic electrodes 420A-420D and cathodic electrodes 422A-422D are different electrodes and unique to the stimulation program.

In the example configuration of FIGS. 7A-7B, external programmer 104 has configured each of the first, second, third, and fourth electrical stimulation therapy programs to deliver electrical pulses at 1200 Hertz. In other words, each pair of electrodes 420 and 422 deliver electrical pulses at 1200 Hertz. Therefore, tissue at the site of each pair of electrodes 420 and 422 receive electrical stimulation pulses at 1200 Hertz within a certain distance from the respective pair of electrodes. FIG. 7B depicts zones of stimulation 710A-710D, which represent zones of tissue stimulation that may be affected by each of the respective pair of electrodes 420A-420D and 422A-422D. As shown in FIG. 7B, some tissue may be affected by stimulation from only one electrode pair while other tissue may be affected by stimulation from two or more of the electrode pairs. For example, some regions of tissue are affected by stimulation from only a single pair of electrodes, and therefore receive electrical stimulation pulses the single electrode pair at 1200 Hertz. For example, tissue region 702 receives electrical stimulation pulses from only electrodes 420B and 422B) at 1200 Hertz.

By interleaving the electrical pulses of each electrical stimulation therapy program, IMD 102 creates a combined electrical pulse train that delivers electrical therapy at a frequency higher than the frequency of each individual pair of electrodes for tissue affected by more than one individual pair of electrodes. For example, regions of tissue 704 lie between two pairs of electrodes. In the example of FIG. 7B, one region of tissue 704 is within both zones of stimulation 710B and 710D. Therefore, region of tissue 704 receives electrical pulses from both the first electrical stimulation program and the second electrical stimulation program originating from each of these cathodes (e.g., 422B and 422D, respectively). Because the first electrical stimulation program and the second electrical stimulation program are interleaved, region of tissue 704 receives a combined electrical pulse train having an effective frequency of 2400 Hertz.

As another example, tissue 706 is within all zones of stimulation 710A, 710B, 710C, and 710D. Thus, region of tissue 706 receives electrical pulses from each of the four electrical stimulation programs originating from each of these cathodes (e.g., 422A-422D respectively). Because the four electrical stimulation programs are interleaved, tissue 706 is affected by and receives a combined electrical pulse train having an effective frequency of 4800 Hertz.

FIGS. 8A-8F are illustrations depicting example configurations for electrodes 116, 118 of the IMD of FIG. 2. In the example of FIGS. 8A-8F, electrodes 116, 118 are configured in a substantially similar fashion to the electrodes depicted by user interface 302 of FIG. 6. Each of the configurations depicted in FIGS. 8A-8F adjust the space between the anode and cathode electrode for each electrical stimulation program. This has the effect of adjusting the spread of the electrical stimulation pulses, which adjusts area of the target tissue area affected by multiple electrical stimulation programs.

In the examples of FIGS. 8A-8F, anodic electrode 420A and cathodic electrode 420A deliver electrical pulses according to the first electrical therapy program. Further, anodic electrode 420B and cathodic electrode 420B deliver electrical pulses according to the second electrical therapy program. Further, anodic electrode 420C and cathodic electrode 420C deliver electrical pulses according to the third electrical therapy program. Further, anodic electrode 420D and cathodic electrode 420D deliver electrical pulses according to the fourth electrical therapy program.

Figure 8A:
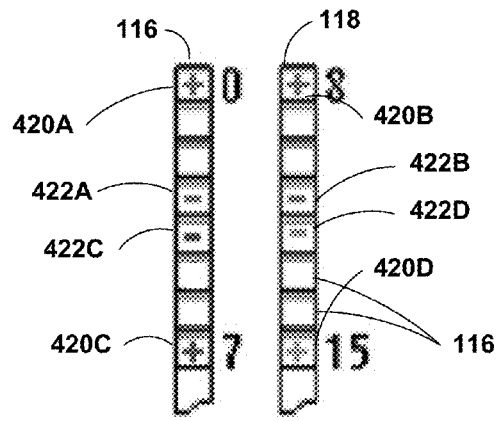
FIGS. 8A-8F are illustrations depicting example configurations for electrodes of the IMD of FIG. 2.

In the example configuration of FIG. 8A, the electrodes 420, 422 are positioned to spread the electrical field of the stimulation pulses to a larger tissue area than is possible with the electrode configuration of FIG. 7. However, in other examples, the electrodes 420, 422 may be positioned to spread the electrical field of the stimulation pulses to a smaller tissue area than is possible with the electrode configuration of FIG. 7. In yet further examples, the electrodes 420, 422 may be positioned to spread the electrical field of the stimulation pulses to an area of tissue that overlaps, at least in part, the tissue area stimulated by the electrode configuration of FIG. 7.

Figure 8B:
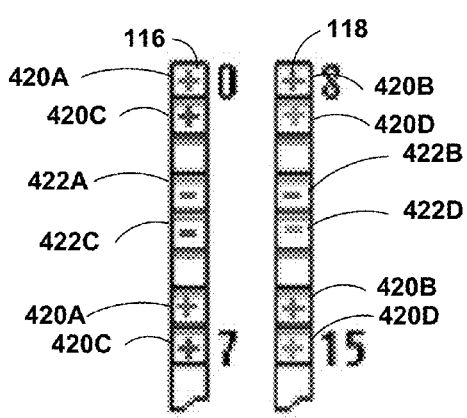

In example configuration of FIG. 8B, the electrodes 420, 422 are positioned to balance the anodic effect above and below the cathode to keep the electrical stimulation field more centrally focused vertically. Further, this configuration increases the current density in the cathode area in comparison to the current density of the anode area to minimize modulation of the tissue or nerves around the anodes.

Figure 8C:
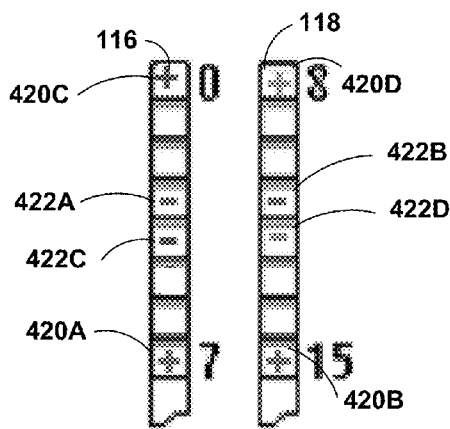

In example configuration of FIG. 8C, the electrodes 420, 422 are positioned to cross over each other vertically. This has the effect of increasing overlap of the cathodic effect more than in configuration 802 and 804.

Figure 8D:
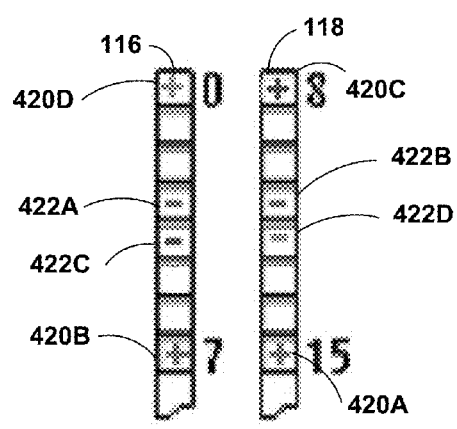

In example configuration of FIG. 8D, the electrodes 420, 422 are positioned to cross the electrical pulses delivered by the electrical therapy programs across the leads. This has the effect of creating a larger overlap of the electrical fields of the electrical pulses between the leads.

Figure 8E:
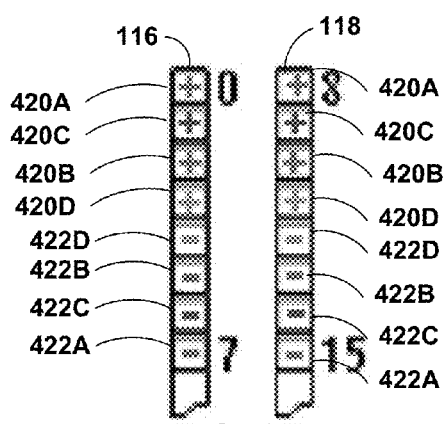

In example configuration of FIG. 8E, the electrodes 420, 422 are positioned to maximizing the overlap of the four electrical therapy programs in the center of one or both leads. This configuration attempts to achieve the highest overlap between the four electrical therapy programs, and thus the highest frequency effect over each of the leads.

Figure 8F:
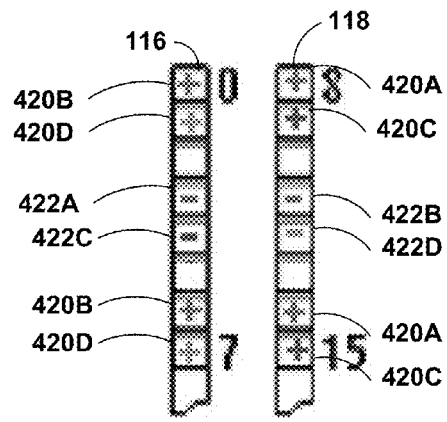

In example configuration of FIG. 8F, the electrodes 420, 422 are positioned in a crossover guarded cathode configuration. This configuration induces a greater cathodic effect in comparison to the anodic effect in the tissue area between the leads.

In the foregoing examples depicted in FIGS. 8A-8F, each of first electrical therapy program, second electrical therapy program, third electrical therapy program, fourth electrical therapy program may use a unique pulse width or a unique pulse rate so as to further change the area of tissue that is affected by the plurality of electrical therapy programs. Therefore, an IMD 102 according to the techniques of the disclosure allows for a clinician to more precisely apply stimulation at varying frequencies to different tissues in a manner not possible with other IMDs that deliver only a single high-frequency electrical stimulation program over a pair of electrodes.

Figure 9:
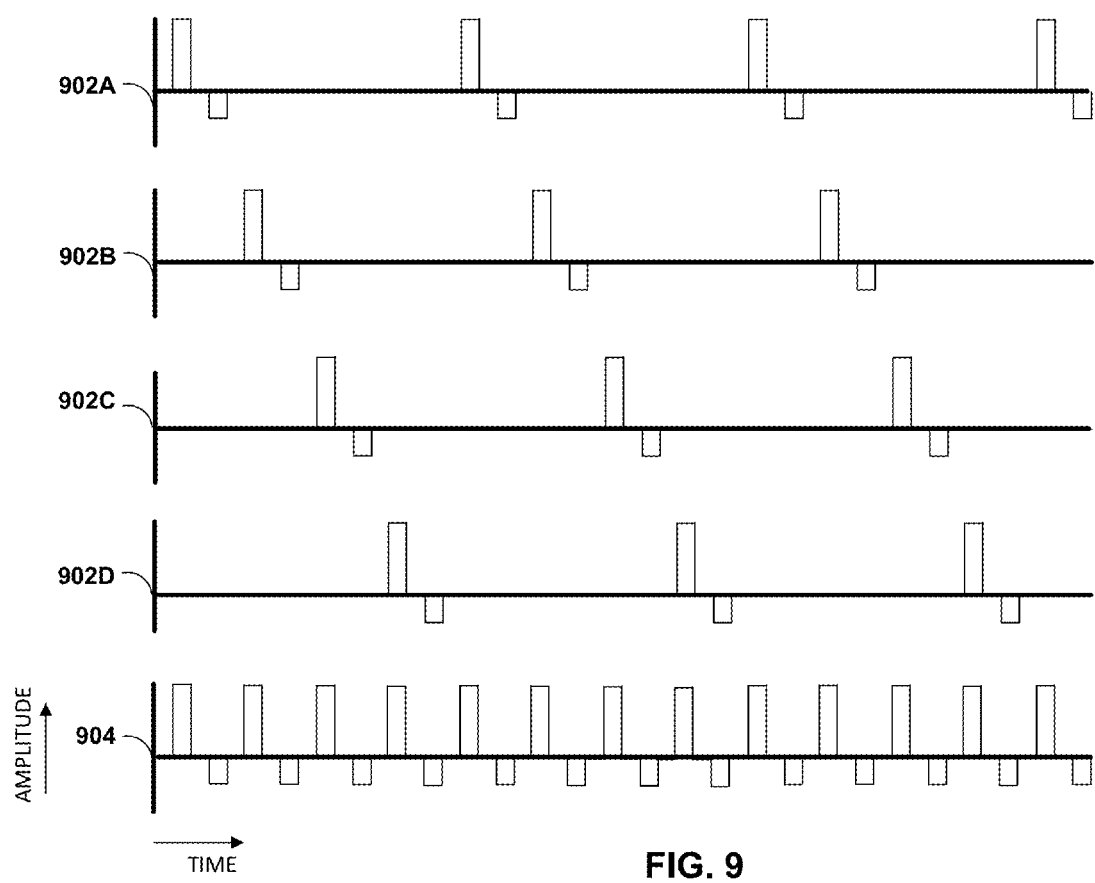
FIG. 9 is a timing diagram illustrating example electrical stimulation pulses according to the techniques of the disclosure.

FIG. 9 is a timing diagram illustrating example electrical stimulation pulses 902A-902D and 904 according to the techniques of the disclosure. For convenience, FIG. 9 is described with reference to the example IMD 102 of FIG. 2.

In the example of FIG. 9, electrode 116A functions as an anode and electrode 118A functions as a cathode to deliver, to a target tissue area of patient 12, a first plurality 902A of electrical stimulation pulses according to a first electrical stimulation therapy program. Similarly, electrode 116B functions as an anode and electrode 118B functions as a cathode to deliver a second plurality 902B of electrical stimulation pulses according to a second electrical stimulation therapy program, electrode 116C functions as an anode and electrode 118C functions as a cathode to deliver a third plurality 902C of electrical stimulation pulses according to a third electrical stimulation therapy program, and electrode 116D functions as an anode and electrode 118D functions as a cathode to deliver a fourth plurality 902D of electrical stimulation pulses according to a fourth electrical stimulation therapy program. Each plurality of electrical stimulation pulses 902A-902D and combined electrical pulse train 904 of FIG. 9 depict an example baseline and example positive and negative amplitudes from the baseline.

In the example of FIG. 9, IMD 102 interleaves the first, second, third, and fourth plurality of electrical stimulation pulses in time so as to alternate delivery of the pulses between the different electrode combinations. Further, each pairing of electrodes 116, 118 is unique to the electrode combination. While in the example of FIG. 9, each electrode combination comprises a single anodic electrode and a single cathodic electrode, in other examples, each electrode combination comprises a plurality of electrodes functioning as anodes and/or a plurality of electrodes functioning as cathodes, and each of these electrodes are unique to each electrode combination.

In the example of FIG. 9, IMD 102 delivers each of the first, second, third, and fourth plurality of electrical stimulation pulses at a frequency of 1200 Hertz. Thus, the tissue proximate to electrodes 116A and 118A, the tissue proximate to electrodes 116B and 118B, the tissue proximate to electrodes 116C and 118C, the tissue proximate to electrodes 116D and 118D receives electrical stimulation pulses at a frequency of 1200 Hertz. However, the target tissue area is subjected to each of the first, second, third, and fourth plurality of electrical stimulation pulses. Therefore, the target tissue area receives a combined electrical pulse train 904 having an effective frequency equal to the sum of the frequencies of the first, second, third, and fourth plurality of electrical stimulation pulses (e.g., 4800 Hertz).

In the example of FIG. 9, the system described is configured to deliver biphasic electrical stimulation pulses. In a biphasic configuration, after delivering a therapy pulse, and prior to delivering a subsequent therapy pulse, the system delivers a concomitant recovery pulse having a polarity opposite to the therapy pulse. Such a configuration evenly distributes electrical charge so as to maintain charge balance in the system. In another example, the system is configured to deliver recovery pulses corresponding to each of the therapy pulses while a therapy pulse is not being delivered by one of the electrical stimulation pulses.

Accordingly, the techniques of the disclosure allow an IMD to deliver higher frequency stimulation using interleaved low-frequency electrical stimulation therapy programs. Such an IMD may provide stimulation at higher rates more effectively than other devices because the tissue near each of the electrodes receive lower frequency stimulation, and thereby less energy, while the targeted tissue area receives the effective high-frequency stimulation. Furthermore, by controlling the frequency or parameters of each of the first, second, third, and fourth plurality of electrical stimulation pulses, a clinician may more precisely control the parameters of the stimulation to the target tissue in a manner not possible with other IMDs that deliver only a single high-frequency electrical stimulation program over a pair of electrodes.

Figure 10:
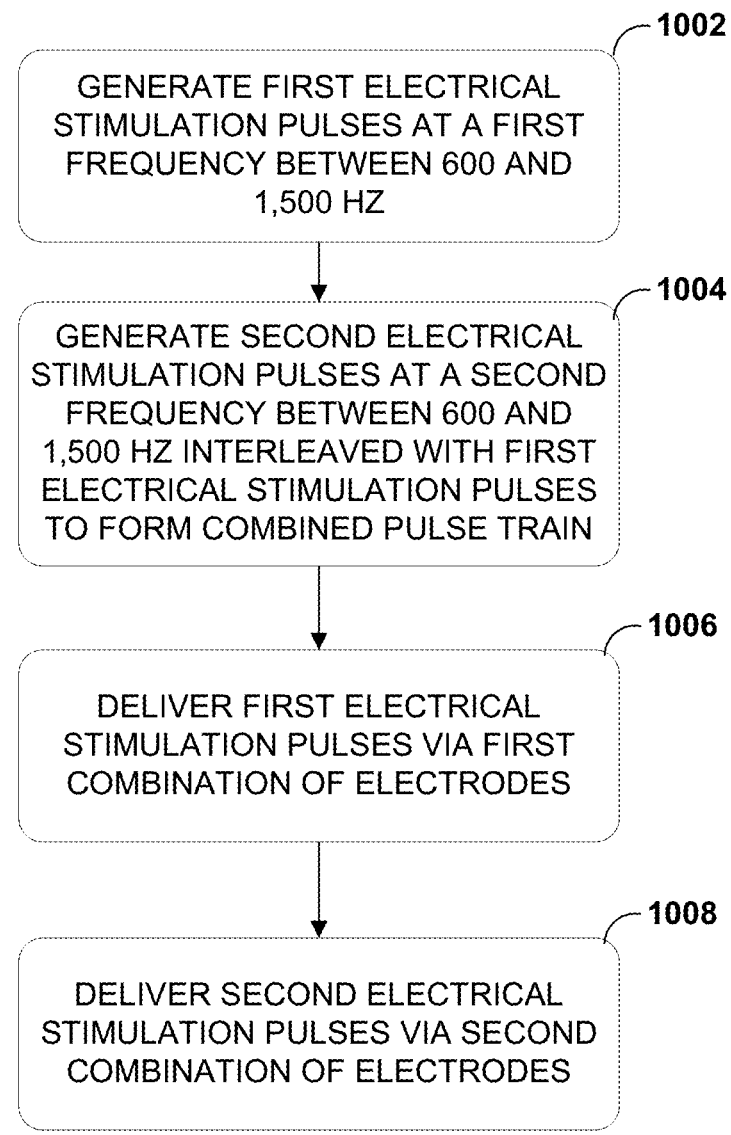
FIG. 10 is a flowchart illustrating an example operation according to the techniques of the disclosure.

FIG. 10 is a flowchart illustrating an example operation according to the techniques of the disclosure. For convenience, FIG. 10 is described with respect to IMD 102 of FIGS. 1 and 2. However, the techniques of FIG. 10 may be performed different components of IMD 102 or by additional or alternative medical devices.

In the example of FIG. 10, a clinician, via external controller 104, issues instructions defining parameters for delivery of electrical stimulation therapy to IMD 102. In response to these instructions, stimulation generator 202 of IMD 102 generates a first plurality of electrical stimulation pulses at a first frequency greater than 600 Hertz and less than 1,500 Hertz (1002). Further, stimulation generator 202 of IMD 102 generates a second plurality of electrical stimulation pulses at a second frequency greater than 600 Hertz and less than 1,500 Hertz on a time-interleaved basis with the first electrical stimulation pulses such that the first and second stimulation pulses form a combined pulse train with a combined pulse frequency of greater than approximately 1,500 Hertz (1004). In some examples, stimulation generator 202 of IMD 102 generates a third plurality of electrical stimulation pulses having a third frequency less than 1,500 Hertz and a fourth plurality of electrical stimulation pulses having a fourth frequency less than 1,500 Hertz. In some examples, stimulation generator 202 of IMD 102 generates an N plurality of electrical stimulation pulses, delivered to the patient via N electrode combinations, wherein "N" is any number, and each of the N plurality electrical stimulation pulses has a frequency less than 1,500 Hertz.

In some examples, the first plurality of electrical stimulation pulses and the second plurality of electrical stimulation pulses each have a frequency of greater than approximately 600 Hertz in some examples, greater than 1,200 Hertz in other examples, and greater than 1400 Hertz in still other examples. Additionally, pulses of each individual plurality of pulses may have a frequency of less than approximately 1,500 Hertz in some examples. In some examples, the frequency may be greater than approximately 600 Hertz and less than approximately 1,500 Hertz, greater than approximately 1,200 Hertz and less than approximately 1,500 Hertz in other examples, and greater than approximately 1,200 Hertz and less than approximately 1,250 Hertz in still other examples. In some examples, the pulses of each individual plurality of pulses have a frequency of approximately 1,200 Hertz.

In some examples, the combined pulse train signal may have a frequency of greater than approximately 1,200 Hertz in some examples, greater than 1,500 Hertz in other examples, greater than 5,000 Hertz in other examples, or greater than 10,000 Hertz in still other examples. Additionally, the combined pulse train signal may have a frequency of less than approximately 20,000 Hertz in some examples, less than 10,000 Hertz in other examples, or less than 5,000 Hertz in still other examples. In some examples, the frequency may be greater than approximately 1,200 Hertz and less than approximately 20,000 Hertz, or greater than approximately 1,200 Hertz and less than approximately 5,000 Hertz in other examples. In some examples, the signal has a frequency of approximately 4,800 Hertz. In a different example, the frequency may be greater than approximately 5,000 Hertz and less than approximately 20,000 Hertz, greater than approximately 5,000 Hertz and less than approximately 10,000 Hertz in other examples, and greater than approximately 10,000 Hertz and less than approximately 20,000 Hertz in still other examples. In some examples, the signal has a frequency of approximately 10,000 Hertz.

Processor 210 of IMD 102 delivers the first electrical stimulation pulses to patient 12 via a first combination of electrodes including at least one anodic electrode 116A and at least one cathodic electrode 118A (1006). Further, processor 210 of IMD 102 delivers the second electrical stimulation pulses to patient 12 via a second combination of electrodes including at least one anodic electrode 116B and at least one cathodic electrode 118B (1008). In the example operation of FIG. 10, none of the second combination of electrodes (e.g., 116B and 118B) are common with any of the electrodes of the first combination of electrodes (e.g. 116A and 118A).

Accordingly, the techniques of the disclosure allow an IMD to deliver higher frequency stimulation using interleaved low-frequency electrical stimulation therapy programs. Such an IMD may provide stimulation at higher rates more effectively than other devices because the tissue near each of the electrodes receive lower frequency stimulation, and thereby less energy, while the targeted tissue area receives the effective high-frequency stimulation. Furthermore, an IMD according to the techniques of the disclosure may allow for a clinician to more precisely apply stimulation at varying frequencies to different tissues in a manner not possible with other IMDs that deliver only a single high-frequency electrical stimulation program over a pair of electrodes.

The techniques described in this disclosure may be implemented, at least in part, in hardware, software, firmware or any combination thereof. For example, various aspects of the described techniques may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A method comprising:
generating first electrical stimulation pulses at a first frequency greater than approximately 600 Hertz and less than approximately 1,500 Hertz;
generating second electrical stimulation pulses at a second frequency greater than approximately 600 Hertz and less than approximately 1,500 Hertz;
generating third electrical stimulation pulses at a third frequency greater than approximately 600 Hertz and less than approximately 1,500 Hertz, wherein the first, second, and third electrical stimulation pulses are generated on a time-interleaved basis with one another such that the first, second, and third electrical stimulation pulses form a combined pulse train with a combined pulse frequency of greater than approximately 1,500 Hertz;
delivering the first electrical stimulation pulses to a patient via a first combination of electrodes including at least one anodic electrode and at least one cathodic electrode;
delivering the second electrical stimulation pulses to the patient via a second combination of electrodes including at least one anodic electrode and at least one cathodic electrode, wherein none of the electrodes of the second combination of electrodes are common with any of the electrodes of the first combination of electrodes; and
delivering the third electrical stimulation pulses to the patient via a third combination of electrodes including at least one anodic electrode and at least one cathodic electrode, wherein none of the electrodes of the third combination of electrodes are common with any of the electrodes of the first or second combinations of electrodes.

2. The method of claim 1, wherein the first frequency, the second frequency, and the third frequency are the same.

3. The method of claim 1, wherein the first frequency, the second frequency, and the third frequency are different from one another.

4. The method of claim 1, further comprising selecting the first combination of electrodes, the second combination of electrodes, and the third combination of electrodes and one or more parameters of the first electrical stimulation pulses, the second electrical stimulation pulses, and the third electrical stimulation pulses such that the combined pulse train is configured to reduce pain of the patient without producing substantial paresthesia in the patient when the first, second, and third electrical stimulation pulses are delivered to a spinal cord of the patient.

5. The method of 4, further comprising delivering the first, second, and third stimulation pulses to the spinal cord of the patient via the first, second, and third combinations of electrodes, respectively.

6. The method of claim 5, wherein the first, second, and third combinations of electrodes are located proximate to a target nerve site of the spinal cord.

7. The method of claim 6, wherein delivering the first, second, and third stimulation pulses to the spinal cord of the patient comprises delivering the first, second, and third stimulation pulses to dorsal column tissue of the spinal cord selected to depolarize neurons without neuronal activation.

8. The method of claim 1,
wherein the first frequency is greater than approximately 1,200 and less than approximately 1,500 Hertz,
wherein the second frequency is greater than approximately 1,200 and less than approximately 1,500 Hertz, and
wherein the third frequency is greater than approximately 1,200 and less than approximately 1,500 Hertz.

9. The method of claim 1,
wherein the first frequency is greater than approximately 1,400 and less than approximately 1,500 Hertz,
wherein the second frequency is greater than approximately 1,400 and less than approximately 1,500 Hertz, and
wherein the third frequency is greater than approximately 1,400 and less than approximately 1,500 Hertz.

10. The method of claim 1, wherein the combined pulse frequency of at least the first and second electrical stimulation pulses is greater than approximately 900 Hertz and less than approximately 1,500 Hertz.

11. The method of claim 1, wherein the combined pulse frequency of at least the first and second electrical stimulation pulses is greater than approximately 1,200 Hertz and less than approximately 20,000 Hertz.

12. The method of claim 11, wherein the combined pulse frequency of at least the first and second electrical stimulation pulses is greater than approximately 1,200 and less than approximately 5,000 Hertz.

13. The method of claim 1, wherein the electrodes are carried in a two-dimensional array on a paddle lead.

14. The method of claim 1, wherein the electrodes are carried on one or more axial leads.

15. The method of claim 1,
wherein the first electrical stimulation pulses have a current amplitude in a range of approximately 0.1 microamps to 25 milliamps, a frequency greater than approximately 600 and less than approximately 1,500 Hertz, and a pulse width in a range of approximately 2 microseconds to 50 microseconds,
wherein the second electrical stimulation pulses have a current amplitude in a range of approximately 0.1 microamps to 25 milliamps, a frequency greater than approximately 600 and less than approximately 1,500 Hertz, and a pulse width in a range of approximately 2 microseconds to 50 microseconds, and
wherein the third electrical stimulation pulses have a current amplitude in a range of approximately 0.1 microamps to 25 milliamps, a frequency greater than approximately 600 and less than approximately 1,500 Hertz, and a pulse width in a range of approximately 2 microseconds to 50 microseconds.

16. The method of claim 1,
wherein the first electrical stimulation pulses have a voltage amplitude in a range of approximately 10 millivolts to 14 Volts, a frequency greater than approximately 600 and less than approximately 1,500 Hertz, and a pulse width in a range of approximately 2 microseconds to 50 microseconds,
wherein the second electrical stimulation pulses have a voltage amplitude in a range of approximately 10 millivolts to 14 Volts, a frequency greater than approximately 600 and less than approximately 1,500 Hertz, and a pulse width in a range of approximately 2 microseconds to 50 microseconds, and
wherein the third electrical stimulation pulses have a voltage amplitude in a range of approximately 10 millivolts to 14 Volts, a frequency greater than approximately 600 and less than approximately 1,500 Hertz, and a pulse width in a range of approximately 2 microseconds to 50 microseconds.

17. The method of claim 1, further comprising:
generating fourth electrical stimulation pulses at a fourth frequency greater than approximately 600 Hertz and less than approximately 1,500 Hertz, wherein the first, second, third, and fourth electrical stimulation pulses are generated on a time-interleaved basis with one another such that the first, second, third, and fourth electrical stimulation pulses form a combined pulse train with a combined pulse frequency of greater than approximately 2,400 Hertz;
and
delivering the fourth electrical stimulation pulses to the patient via a fourth combination of electrodes including at least one anodic electrode and at least one cathodic electrode, wherein none of the electrodes of the fourth combination of electrodes are common with any of the electrodes of the first, second, or third combinations of electrodes.

18. The method of claim 1, wherein each of the first combination of electrodes, the second combination of electrodes, and the third combination of electrodes is positioned to balance an anodic effect above and below the at least one anodic electrode of the first combination of electrodes.

19. A system comprising:
at least one lead comprising:
a first combination of electrodes including at least one anodic electrode and at least one cathodic electrode; and
a second combination of electrodes including at least one anodic electrode and at least one cathodic electrode, wherein none of the electrodes of the second combination of electrodes are common with any of the electrodes of the first combination of electrodes;
a third combination of electrodes including at least one anodic electrode and at least one cathodic electrode, wherein none of the electrodes of the third combination of electrodes are common with any of the electrodes of the first or second combinations of electrodes; and an implantable medical device (IMD) comprising:
  stimulation generation circuitry configured to:
    generate first electrical stimulation pulses at a first frequency greater than approximately 600 Hertz and less than approximately 1,500 Hertz;
    generate second electrical stimulation pulses at a second frequency greater than approximately 600 Hertz and less than approximately 1,500 Hertz;
    generating third electrical stimulation pulses at a third frequency greater than approximately 600 Hertz and less than approximately 1,500 Hertz, wherein the stimulation generation circuitry is further configured to generate the first, second, and third electrical stimulation pulses on a time-interleaved basis with one another such that the first, second, an third electrical stimulation pulses form a combined pulse train with a combined pulse frequency of greater than approximately 1,500 Hertz; and
  processing circuitry configured to:
    control delivery of the first electrical stimulation pulses to a patient via the first combination of electrodes;
    control delivery of the second electrical stimulation pulses to the patient via the second combination of electrodes; and
    control delivery of the third electrical stimulation pulses to the patient via the third combination of electrodes.

20. The system of claim 19,
  wherein the first frequency is greater than approximately 1,200 and less than approximately 1,500 Hertz,
  wherein the second frequency is greater than approximately 1,200 and less than approximately 1,500 Hertz, and
  wherein the third frequency is greater than approximately 1,200 and less than approximately 1,500 Hertz.

21. The system of claim 19, wherein the combined pulse frequency of at least the first and second electrical stimulation pulses is greater than approximately 1,200 Hertz and less than approximately 5,000 Hertz.

22. The system of claim 19,
  wherein the stimulation generation circuitry is further configured to:
    generate fourth electrical stimulation pulses at a fourth frequency greater than approximately 600 Hertz and less than approximately 1,500 Hertz, wherein the first, second, third, and fourth electrical stimulation pulses are generated on a time-interleaved basis with one another such that the first, second, third, and fourth stimulation pulses form a combined pulse train with a combined pulse frequency of greater than approximately 2,400 Hertz; and
  wherein the processing circuitry is further configured to:
    control delivery of the fourth electrical stimulation pulses to the patient via a fourth combination of electrodes including at least one anodic electrode and at least one cathodic electrode, wherein none of the electrodes of the fourth combination of electrodes are common with any of the electrodes of the first, second, or third combinations of electrodes.

* * * * *